United States Patent
Alfano et al.

(10) Patent No.: US 6,665,557 B1
(45) Date of Patent: Dec. 16, 2003

(54) SPRECTROSCOPIC AND TIME-RESOLVED OPTICAL METHODS AND APPARATUS FOR IMAGING OBJECTS IN TURBED MEDIA

(75) Inventors: Robert R. Alfano, Bronx, NY (US); Swapan Kumar Gayen, Marlboro, NJ (US); Manuel E. Zevallos, Jackson Heights, NY (US)

(73) Assignee: The Research Foundation of City College of New York, New York, NY (US)

(*) Notice: Subject to any disclaimer, the term of this patent is extended or adjusted under 35 U.S.C. 154(b) by 134 days.

(21) Appl. No.: 09/597,505

(22) Filed: Jun. 20, 2000

Related U.S. Application Data

(60) Provisional application No. 60/171,066, filed on Dec. 16, 1999, and provisional application No. 60/168,413, filed on Dec. 1, 1999.

(51) Int. Cl.$^7$ ................................................. A61B 6/00
(52) U.S. Cl. ...................................... 600/473; 600/475
(58) Field of Search ................................. 600/473, 476, 600/310, 322, 323, 328, 475; 356/40

(56) References Cited

U.S. PATENT DOCUMENTS

| | | | |
|---|---|---|---|
| 5,371,368 A | | 12/1994 | Alfano et al. |
| 5,719,399 A | | 2/1998 | Alfano et al. |
| 5,799,656 A | * | 9/1998 | Alfano et al. ............ 600/473 |
| 5,847,394 A | | 12/1998 | Alfano et al. |
| 5,853,370 A | * | 12/1998 | Chance et al. ............ 600/473 |
| 5,931,789 A | | 8/1999 | Alfano et al. |

\* cited by examiner

*Primary Examiner*—Shawna J. Shaw
(74) *Attorney, Agent, or Firm*—Kriegsman & Kriegsman

(57) ABSTRACT

Method and apparatus for imaging objects in turbid media. In one embodiment, the method comprises illuminating at least a portion of the turbid medium with substantially monochromatic light of at least two wavelengths in the 600–1500 nm spectral range. A first of the at least two wavelengths is equal to a resonance wavelength for an optical property of an object in the illuminated portion of the turbid medium but is not equal to a resonance wavelength for the turbid medium. A second of the at least two wavelengths is not equal to a resonance wavelength for either the object or the turbid medium. Light emergent from the turbid medium following each of the foregoing illuminations comprises a ballistic component, a snake component and a diffuse component. A direct shadowgram image may be obtained by preferentially passing from the emergent light, following each illumination. the ballistic and snake components thereof and detecting the preferentially passed light. Alternatively, an inverse reconstruction image may be obtained by determining, following each illumination, the intensity of the diffuse component at a plurality of points in time and then using these pluralities of intensity determinations and a mathematical inversion algorithm to form an image of the object in the turbid medium. An image of the object with higher contrast and better quality may be obtained by using the ratio or difference of the images recorded with resonant light and non-resonant light.

48 Claims, 13 Drawing Sheets

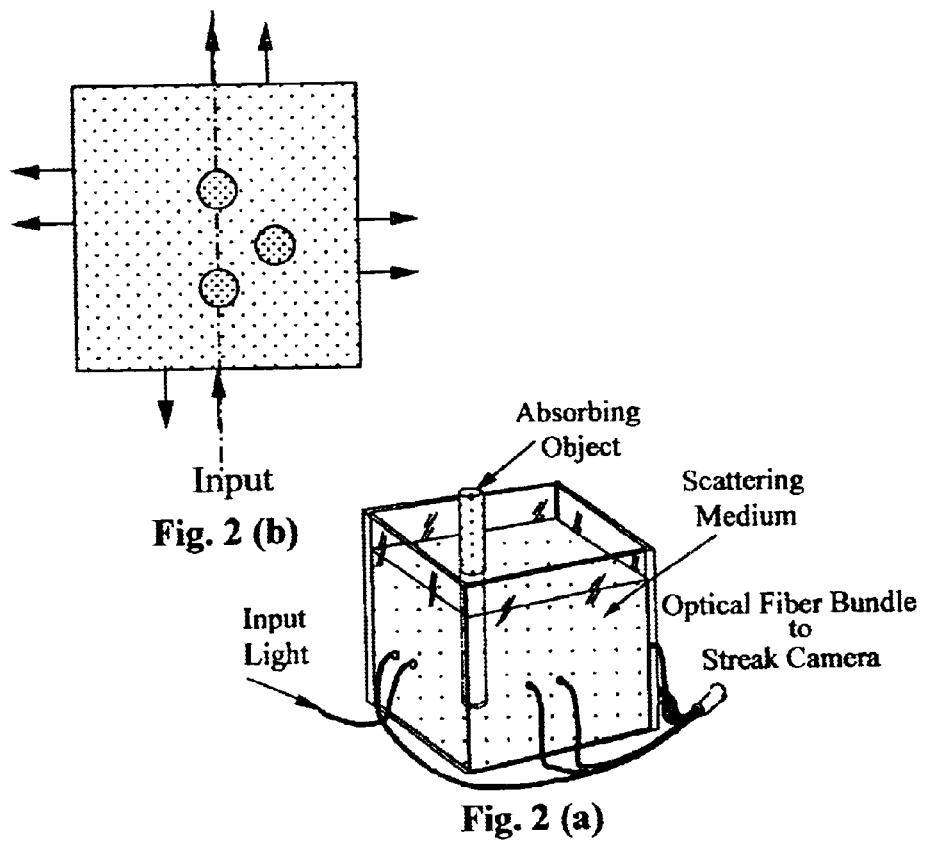
Fig. 2 (b)
Fig. 2 (a)
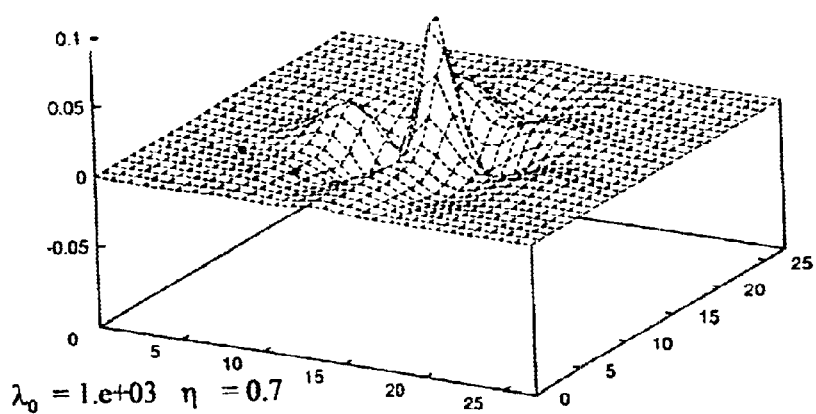
$\lambda_0 = 1.e+03 \quad \eta = 0.7$
Fig. 2 (c)

SPRECTROSCOPIC AND TIME-RESOLVED OPTICAL METHODS AND APPARATUS FOR IMAGING OBJECTS IN TURBED MEDIA

CROSS-REFERENCE TO RELATED APPLICATIONS

The present application claims the benefit under 35 U.S.C. §119(e) of U.S. Provisional Patent Application Ser. No. 60/171,066, filed Dec. 16, 1999, and of U.S. Provisional Patent Application Ser. No. 60/168,413, filed Dec. 1, 1999, the disclosures of both of which are herein incorporated by reference.

STATEMENT REGARDING FEDERALLY SPONSORED RESEARCH OR DEVELOPMENT

This invention was made with Government support under Contract No. NAG5-6952 awarded by NASA. The Government may have certain rights in this invention.

BACKGROUND OF THE INVENTION

The present invention relates generally to methods and apparatuses for imaging objects in turbid media and relates more particularly to a novel method and apparatus for imaging objects in turbid media.

As can readily be appreciated, there are many situations in which the detection of an object in a turbid, i.e., highly scattering, medium is highly desirable. For instance, the detection of a plane in fog is highly desirable for obvious reasons. In addition, the detection of a tumor within an organ of the human body, such as the breast, is advantageous since the early detection of said tumor is useful in devising effective treatment protocols. Although X-ray techniques do provide some measure of success in detecting objects in turbid media, they are not well-suited for detecting very small objects, e.g., tumors less than 1 mm in size, or for detecting objects in thick media. In addition, X-ray radiation can present safety hazards to a person exposed thereto. Other tumor detection techniques involving the use of ultrasound, magnetic resonance and radio isotopes are similarly limited in their detection capabilities and/or create safety concerns.

An alternative technique used to detect objects in turbid media, particularly tumors in the body, is direct shadowgram imaging. Historically, in direct shadowgram imaging, visible or near infrared (NIR) light is incident on one side of a medium, and the transmitted light emergent from the opposite side of the medium is used to form a transillumination image. Alternatively, the backward propagating light emergent from the same side of the medium may be used to form a back-propagation image. A difference in optical properties, such as absorption, emission, or scattering between the object and the turbid medium, provides the basis for the formation of an image. Objects embedded in the medium typically absorb the incident light and appear in the image as shadows. Unfortunately, the usefulness of traditional direct shadowgram imaging as a detection technique is severely limited in those instances in which the medium is thick or the object is very small. This is because light scattering within the medium contributes to noise and reduces the intensity of the unscattered light used to form the shadow image.

To improve the detectability of small objects located in a turbid medium using direct shadowgram imaging, many investigators have attempted to selectively use only certain components of the transilluminating (or back-propagating) light signal. This may be done by exploiting the properties of photon migration through a scattering medium. Photons migrating through a turbid medium have traditionally been categorized into three major signal components: (1) the ballistic (coherent) photons which arrive first by traveling over the shortest, most direct path; (2) the snake (quasi-coherent) photons which scatter only slightly and arrive after the ballistic photons and which deviate, only to a very slight extent, off a straight-line propagation path; and (3) the diffusive (incoherent) photons which experience comparatively more scattering than do ballistic and snake photons and, therefore, deviate more considerably from the straight-line propagation path followed by ballistic and snake photons.

Because the ballistic and snake photons represent comparatively less distorted image information than do the diffusive photons, one approach to improving direct shadowgram imaging has been to selectively use the ballistic and snake photons to form the shadowgram image. This typically involves using various space-gating, time-gating or space/time-gating techniques to permit the detection of ballistic and snake photons, while rejecting diffusive photons. Examples of this approach are disclosed in the following patents and publications, the disclosures of which are incorporated herein by reference: U.S. Pat. No. 5,140,463, inventors Yoo et al., which issued Aug. 18, 1992; U.S. Pat. No. 5,143,372, inventors Alfano et al., which issued Aug. 25, 1992; U.S. Pat. No. 5,227,912, inventors Ho et al., which issued Jul. 13, 1993; U.S. Pat. No. 5,371,368, inventors Alfano et al., which issued Dec. 6, 1994; U.S. Pat. No. 5,644,429, inventors Alfano et al., which issued Jul. 1, 1997; U.S. Pat. No. 5,710,429, inventors Alfano et al., which issued Jan. 20, 1998; U.S. Pat. No. 5,719,399, inventors Alfano et al., which issued Feb. 17, 1998; Gayen et al., "Sensing lesions in tissues with light," *Optics Express*, 4:475–80 (1999); Gayen et al., "Two-dimensional near-infrared transillumination imaging of biomedical media with a chromium-doped forsterite laser," *Appl. Opt.*, 37:5327–36 (1998); Gayen et al., "Near-infrared laser spectroscopic imaging: a step towards diagnostic optical imaging of human tissues," *Lasers in the Life Sciences*, 37:187–198 (1999); Gayen et al., "Time-sliced transillumination imaging of normal and cancerous breast tissues," *OSA Trends in Optics and Photonics Series Vol. 21 on Advances in Optical Imaging and Photon Migration* ('98), pages 63–66 (1998), edited by J. G. Fujimoto and M. S. Patterson, Optical Society of America; Dolne et al., "IR Fourier space gate and absorption imaging through random media," *Lasers in the Life Sciences*, 6:131–41 (1994); Das et al., "Ultrafast time-gated imaging in thick tissues: a step toward optical mammography," *Opt. Lett.*, 18:1002–03 (1993); Hebden et al., "Time-resolved imaging through a highly scattering medium," *Appl. Opt.*, 30:788–94 (1991); Demos et al., "Time-resolved degree of polarization for human breast tissue," *Opt. Commun.*, 124:439–42 (1996).

An alternative approach to the direct shadowgram imaging techniques described above has been to make use of the diffusive photons which, although containing comparatively less of the direct signal information than the ballistic and snake photons, are more abundant than the ballistic and snake photons. An example of such a technique that makes use of the diffusive photons for imaging involves inverting the experimental scattering data obtained from various points in the medium using an inverse reconstruction algorithm. Examples of inverse reconstruction techniques are disclosed in the following patents and publications, all of which are incorporated herein by reference: U.S. Pat. No. 5,931,789, inventors Alfano et al.. which issued Aug. 3, 1999; U.S. Pat. No. 5,813,988, inventors Alfano et al., which issued Sep. 29, 1998; Cai et al., "Optical tomographic image reconstruction from ultrafast time-sliced-transmission measurements," *Appl. Opt.*, 38:4237–46 (1999); Cai et al., "Time-resolved optical diffusion tomographic image reconstruction in highly scattering turbid media," *Proc. Natl. Acad. Sci. USA*, 93:13561–4 (1996); Arridge, "The Forward and Inverse Problems in Time Resolved Infra-Red Imaging," in *Medical Optical Tomography: Functional Imaging and Monitoring*, SPIE, Vol. IS11, G. Muller ed., 31–64 (1993); Singer et al., "Image Reconstruction of the Interior of Bodies That Diffuse Radiation," *Science*, 248:990–3 (1993); Barbour et al., "A Perturbation Approach for Optical Diffusion Tomography Using Continuous-Wave and Time-Resolved Data," *Medical Optical Tomography: Functional Imaging and Monitoring SPIE Institutes*, Vol. IS11, G. Muller ed., 87–120 (1993); and J. Schotland et al., *App. Opt.*, 32:448 (1993).

Although the various approaches described above have enjoyed some measure of success, there is considerable room for additional improvements.

SUMMARY OF THE INVENTION

It is an object of the present invention to provide a new method and apparatus for imaging objects in turbid media.

It is another object of the present invention to provide a method and apparatus as described above that represents an improvement in image quality with respect to existing direct shadowgram and inverse reconstruction imaging techniques.

It is still another object of the present invention to provide a method and apparatus as described above that has applicability in the detection of tumors and other abnormalities in human body parts, such as the breast, brain, bladder, blood, bones, cervix, aerodigestive tract, artery, liver, prostate and skin.

It is still yet another object of the present invention to provide a method and apparatus that does not involve the use of X-rays or other ionizing. radiation.

The present invention is based, in part, on the principle that the light absorption and light scattering properties of normal and diseased tissues are distinguishable when illuminated at appropriate illuminating wavelengths and that such differences can be exploited to detect tumors (or other lesions) inside the tissue using optical imaging techniques, such as direct shadowgram imaging and inverse reconstruction imaging.

Accordingly, a prerequisite to performing the present technique is to determine the appropriate wavelength(s) at which such differences are apparent between the normal and diseased tissues. This may be done, for example, by observing the optical properties of the various tissues while illuminating the tissues at a variety of different wavelengths, for example, by illuminating the tissues with an illuminating source whose output wavelength is tunable over a broad wavelength range. Examples of optical properties which may be wavelength-dependent include absorption mean. free path $l_a$, scattering mean free path $l_s$, and transport mean free path $l_t$. Two different types of tissues, two different types of tissue components, or a normal tissue and a tumor will have the same values for the aforementioned optical properties over most wavelengths but will have substantially different values for one or more particular wavelengths. Benign tumors and malignant tumors may also be distinguishable at certain wavelengths.

In one embodiment, the method comprises illuminating at least a portion of the turbid medium with substantially monochromatic light of at least two wavelengths in the 600–1500 nm spectral range. A first of the at least two wavelengths is equal to a resonance wavelength for an optical property of an object in the illuminated portion of the turbid medium but is not equal to a resonance wavelength for the turbid medium. A second of the at least two wavelengths is not equal to a resonance wavelength for either the object or the turbid medium. Light emergent from the turbid medium following each of the foregoing illuminations comprises a ballistic component, a snake component and a diffuse component. A direct shadowgram image may be obtained by preferentially passing from the emergent light, following each illumination, the ballistic and snake components thereof and detecting the preferentially passed light. Direct shadowgram images with better contrast may be obtained by using the ratio or difference of the shadowgram images recorded at the resonant and nonresonant wavelengths.

Alternatively, an inverse reconstruction image may be obtained by determining, following each illumination, the intensity of the diffuse component at a plurality of points in time and then using these pluralities of intensity determinations and a mathematical inversion algorithm to form an image of the object in the turbid medium.

Yet another way of obtaining an inverse reconstruction image is to use a sequence of two-dimensional (2-D) images recorded using different temporal intervals (or "slices") of the light emergent (transmission and back-propagation) from the sample, and a mathematical inversion algorithm to form an image of the object in the turbid medium. The 2-D images are spatial intensity distributions of emergent light at different points in time, $I(x,y,t)$, of the emergent light, and the reconstructed image is a three-dimensional (3-D) image that not only detects the object but also provides its location.

An important feature of this invention is that images recorded using light of a resonance wavelength of an optical property of an object inside a turbid medium (or of a constituent of the turbid medium) can be used to map the spatial distribution of the object within the medium (or of the constituent with that specific property within the medium). For example, images of the female human breast obtained using light in the wavelength range of 1120–1240 nm can be used to map the distribution of fatty tissue therewithin ("a fat tree"). Similarly, imaging with light in the 650–780 nm range can be used to map the deoxyhemoglobin (Hb) distribution within the breast ("a deoxyhemoglobin tree"), imaging with light in the 820–900 nm range can be used to map the oxyhemoglobin ($HbO_2$) distribution within the breast ("an oxyhemoglobin tree") and imaging with light in the 940–1010 nm and 1400–1500 nm ranges can be used to map the water distribution in the breast ("a water tree").

Obtaining the ratio or difference of 2-D (or 3-D) images recorded using a resonant wavelength and a non-resonant wavelength will provide 2-D (or 3-D) maps of the optical property to which said resonant wavelength is resonant with, and the images thus obtained will have a much higher contrast than those obtained using a single wavelength.

A particularly useful application of the above-alluded to spectroscopic difference imaging technique is to use the changes in absorption by oxyhemoglobin and deoxyhemoglobin for monitoring blood oxygenation, which enables monitoring of body function. As seen below in FIG. 1(b), the isobestic point where the absorption coefficients of oxyhemoglobin and deoxyhemoglobin are equal is around 800 nm. At shorter wavelengths in the 670–790 nm range, the absorption coefficient of deoxyhemoglobin is significantly higher than that of oxyhemoglobin while at longer wavelengths (810–900 nm), oxyhemoglobin has a higher absorption coefficient than does deoxyhemoglobin. The spectroscopic difference image obtained by subtracting an image recorded at 800 nm (isobestic point) from one recorded at a wavelength with significantly higher absorption by Hb (670–790 nm range) can be used to provide the Hb distribution with higher contrast than a single image recorded using a wavelength in this range. Similarly, the spectroscopic difference image obtained by subtracting an image recorded at 800 nm from one recorded at a wavelength with significantly higher absorption by $HbO_2$ (810–900 nm range) can be used to provide the $HbO_2$ distribution with higher contrast than an image obtained using light of a wavelength in the range.

The illumination of the turbid medium and the detection of the desired components of the emergent light can be performed in either a transmission geometry or a backscattering geometry.

Additional objects, as well as features, aspects and advantages of the present invention, will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference numerals represent like parts:

FIGS. 2(a) and 2(b) are schematic perspective and section views, respectively, of the experimental setup disclosed in Cai et al., "Time-resolved optical diffusion tomographic image reconstruction in highly scattering turbid media," Proc. Natl. Acad. Sci. USA, 93:13561–4 (1996);

FIG. 2(c) is an inverse reconstructed image obtained using the experimental setup of FIGS. 2(a) and 2(b);

FIGS. 6(a) through 6(e) are two-dimensional shadowgram images and accompanying spatial intensity profiles integrated over the same highlighted horizontal area of the specimen of FIG. 6 obtained using the apparatus of FIG. 5 with illumination wavelengths from the Cr:forsterite laser of (a) 1225 nm; (b) 1235 nm; (c) 1255 nm; (d) 1285 nm; and (e) 1300 nm, respectively;

FIGS. 8(a) through 8(d) are spectroscopic images (left frame) and corresponding spatial intensity profiles (right frame) of the specimen of FIG. 8 obtained using the apparatus of FIG. 5 with illumination wavelengths of (a) 1210 nm; (b) 1225 nm; (c) 1275 nm; and (d) 1300 nm, respectively;

DETAILED DESCRIPTION OF PREFERRED EMBODIMENTS

The present invention is based on the discovery that different kinds of materials have wavelength-dependent differences with respect to various optical properties (e.g., absorption coefficient, scattering coefficient, transport mean free path and index of refraction) and that these wavelength-dependent differences can be exploited to image objects in turbid media with higher contrast.

An important application of the imaging technique of the present invention is in the detection of tumors, particularly in the detection of tumors in human breast tissue. The key components of a normal adult female human breast are glandular tissue, fibrous tissue, adipose (fat) tissue, blood vessels, ducts, and nerves. Breast lesions include carcinomas that are malignant, as well as benign tumors, such as fibrodenomas, cysts, lipomas, and mastitis. The most abundant constituent of tissues, in general, is water. One of the key issues in breast imaging is to distinguish between benign and malignant tumors. Salient features in a breast image, such as the number, size, shape and arrangement of calcifications therein, may be indicative of cancer. Differences in optical and spectroscopic properties between the constituents and lesions are necessary for diagnostic optical imaging of breast lesions. The wavelength of light used for imaging is a key parameter since different wavelengths can highlight different constituents in the breast or the organ being imaged.

Figure 1A:
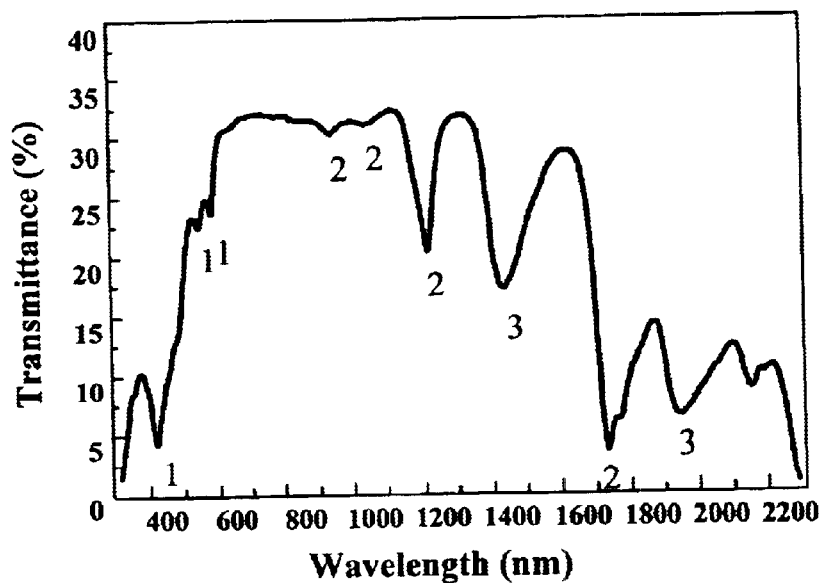
FIG. 1(a) is a graphic representation of an optical transmission spectrum for a 3 mm thick slab of human breast tissue (the labeled absorption resonances are for oxyhemoglobin (1), fat (2) and water (3))
Figure 1B:
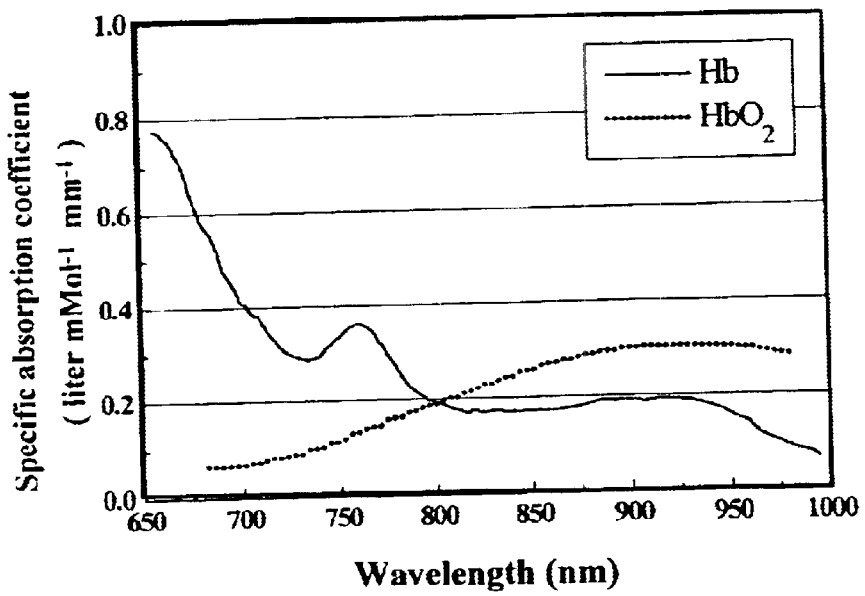
FIG. 1(b) is a graphic representation of the respective absorption coefficients of deoxyhemoglobin (Hb) and oxyhemoglobin (HbO) as a function of wavelength over the 650–1000 nm range.

FIG. 1(a) shows an optical transmission spectrum of a 3 mm thick human female breast specimen showing absorption resonances due to different tissue constituents, namely, oxyhemoglobin, fat and water. (FIG. 1(b) shows the respective absorption coefficients of deoxyhemoglobin (Hb) and oxyhemoglobin (HbO) as a function of wavelength over the 650–1000 nm range.) As can be seen, light attenuation by fatty tissue extends from about 1120–1240 nm with a maximum at 1203 nm. In the experimental setup used to obtain spectroscopic images, a Cr-doped forsterite laser tunable over the NIR spectral range of 1150–1350 nm was used as the light source to tune in and out of that absorption band and obtain images at different wavelengths. A Fourier space gate and a polarization gate were used for sorting out image-bearing light, and a near-infrared area camera was used for forming an image with the sorted light.

FIGS. 2(a) and 2(b) are schematic perspective and section views, respectively, of the experimental setup disclosed in Cai et al., "Time-resolved optical diffusion tomographic image reconstruction in highly scattering turbid media," Proc. Natl. Acad. Sci. USA, 93:13561–4 (1996), and FIG. 2(c) is an inverse reconstructed image obtained using the experimental setup of FIGS. 2(a) and 2(b). As will be seen below, the present invention can be used to improve the contrast of images, such as that of FIG. 2(c).

Figure 3A:
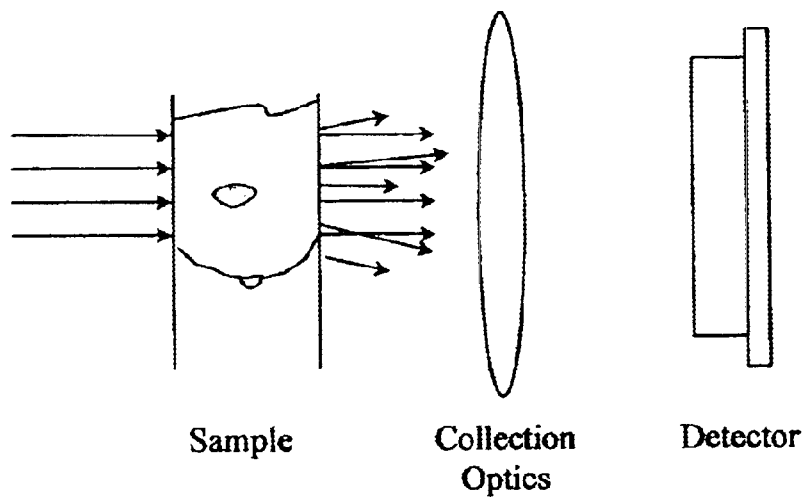
FIGS. 3(a) and 3(b) are schematic diagrams of the arrangements for shadowgram imaging in transmission and backscattering geometries, respectively.
Figure 3B:
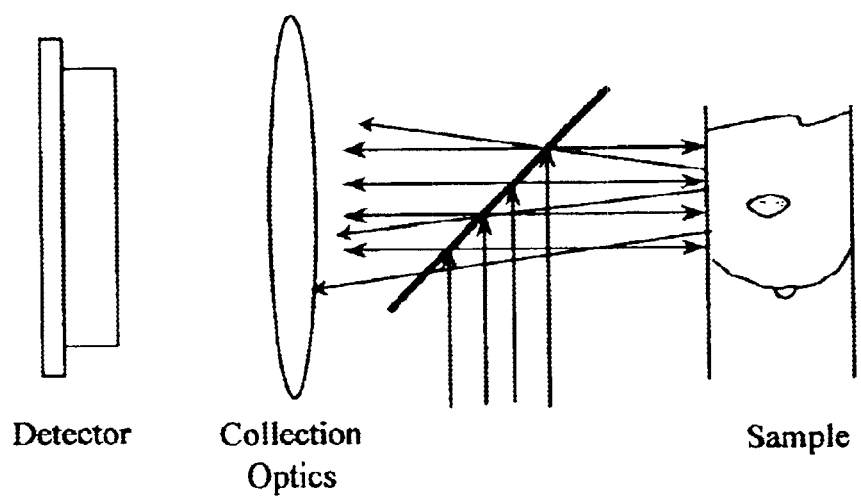
Figure 4C:
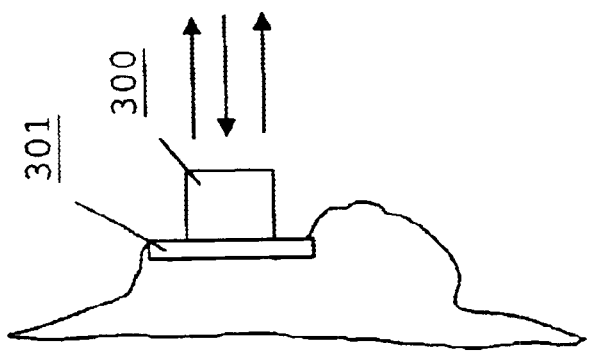
FIGS. 4(a) through 4(c) are schematic diagrams of various arrangements for the direct imaging of a breast in a backscattering geometry.
Figure 4B:
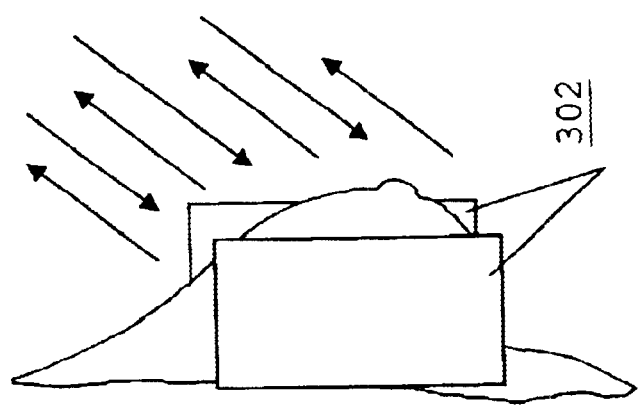
Figure 4A:
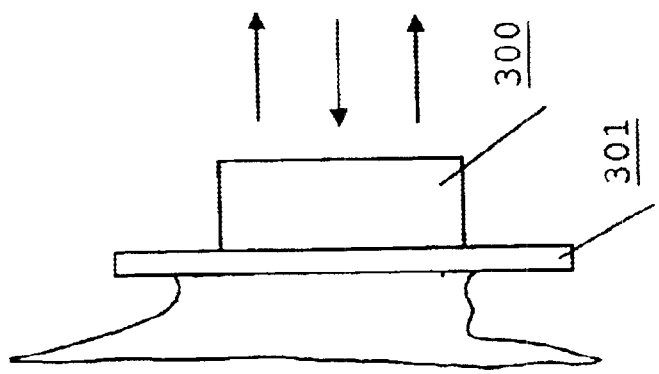

Conventional direct shadowgram imaging typically involves positioning the illuminating source and the detectors in a transmission geometry. relative to the specimen. An alternative approach would be to use a backscattering geometry for both direct shadowgram imaging and inverse tomographic reconstruction. In a backscattering geometry, the detectors collect the light scattered backwards, that is, in a direction opposite to the incident direction. A schematic diagram of the illumination and detection schemes for transmission and backscattering geometries are shown in FIGS. 3(a) and 3(b), respectively. Different configurations of illumination and detection schemes for breast imaging using backscattering geometries are shown schematically in FIGS. 4(a) through 4(c). FIG. 4(a) shows the breast pressed against the chest by a flat transparent plate and the detector collecting the light that is scattered backwards. FIG. 4(b) illustrates the breast being pressed between transparent plates, as is done in x-ray mammography, and the light being incident on the breast and scattered light being collected through the same plate. FIG. 4(c) shows the same arrangement as in FIG. 4(a), except that the detector is small, and data is collected over small areas of the breast allowing for 3-D tomographic reconstruction of local areas of the breast. A backscattering geometry is expected to provide better spatial resolution for direct shadowgram images when the tumor or other structures are closer to the plate through which light is incident. Tomographic inverse reconstruction using a backscattering geometry is expected to provide more precise depth resolution than tomographic inverse reconstruction performed using a transmission geometry. See Cai et al., "Time-resolved optical backscattering model in highly scattering media," Opt. Lett., 23:983–5 (1998).

That which is common both to a direct shadowgram imaging approach and to a tomographic inverse reconstruction imaging approach, in accordance with the teachings of the present invention, is the exploitation of a difference in the spectroscopic characteristics. between the object and the turbid medium at one or more wavelengths.

Figure 5:
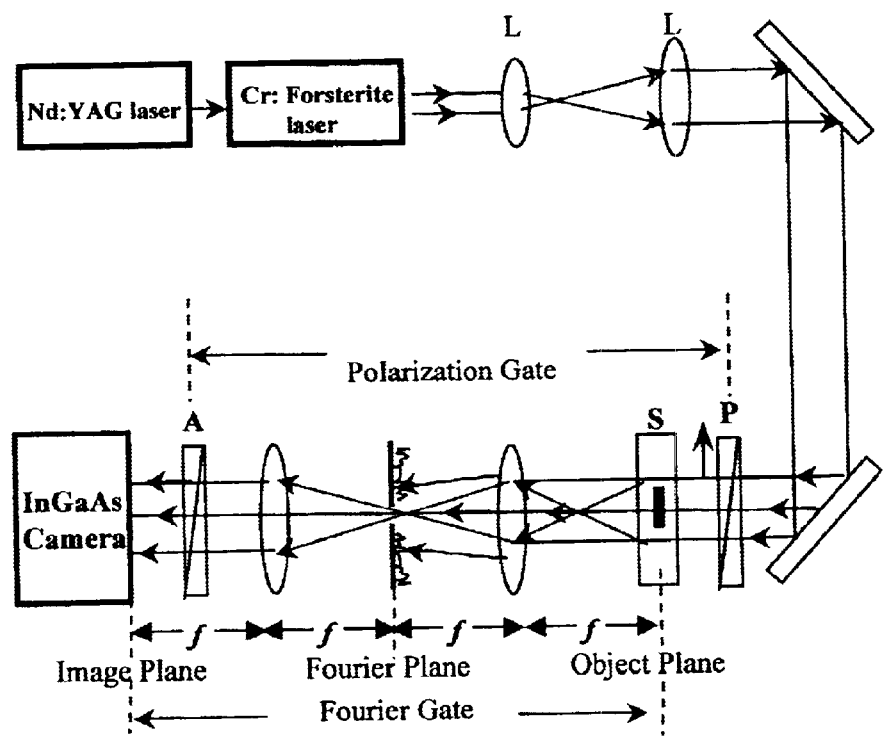
FIG. 5 is a schematic diagram of a first embodiment of an imaging apparatus constructed according to the teachings of the present invention.
Figure 6:
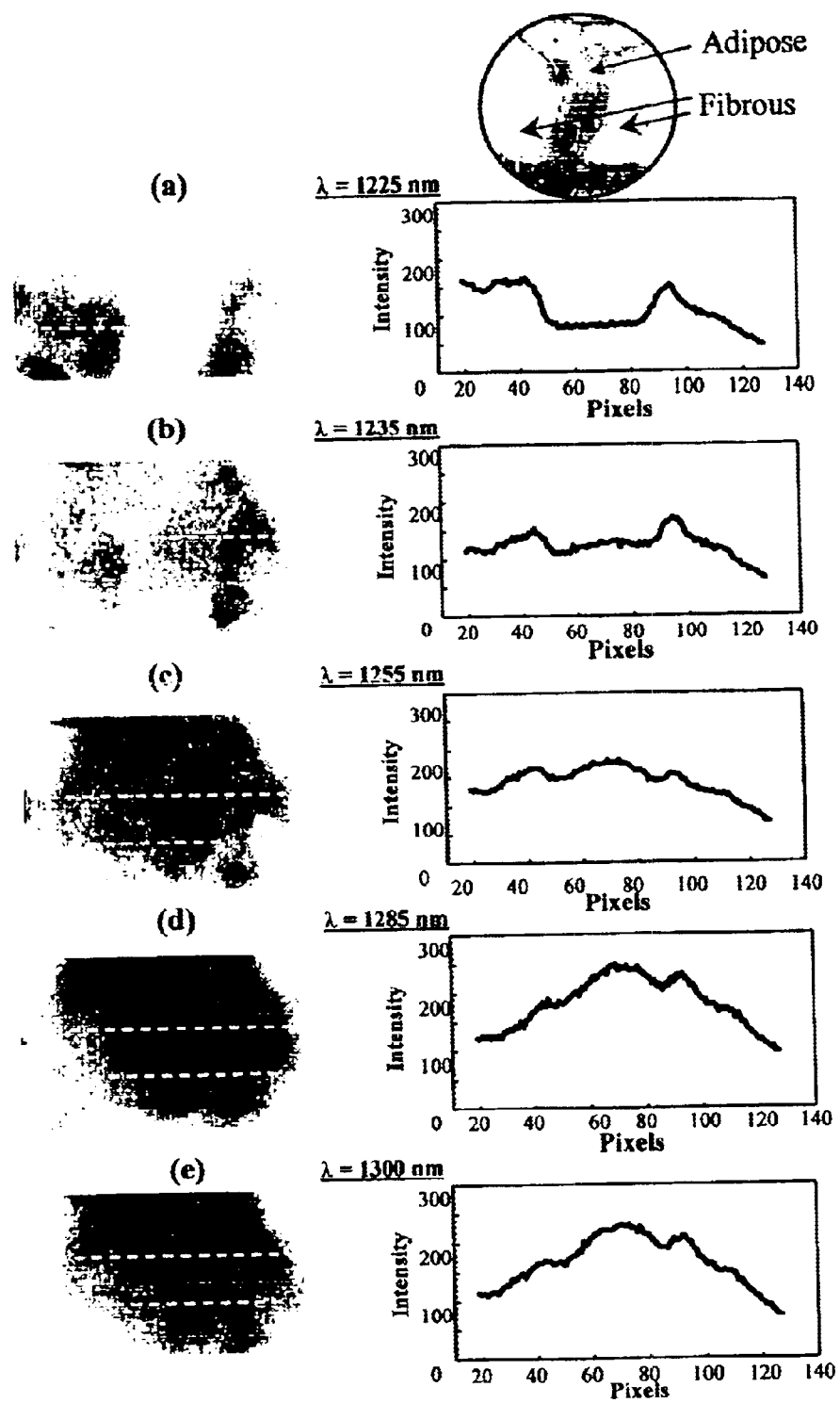
FIG. 6 is a photograph of the exit surface of a 5 mm thick human breast tissue specimen comprising adipose and fibrous regions.

An experimental near-infrared (NIR) spectroscopic imaging apparatus used to demonstrate the principles of the present invention is displayed schematically in FIG. 5. In said apparatus, the continuous-wave (CW) mode-locked output of a $Cr^{4+}$: forsterite laser pumped by a Nd:YAG laser was expanded to an approximately 75 mm diameter beam, and a 35 mm diameter central part of it was used to illuminate the sample. The laser was tuned from 1225 nm to 1300 nm using an intracavity birefringent plate. The output wavelength was monitored with an optical spectrum analyzer. The average power output was maintained at approximately 35 mW for all the wavelengths using appropriate neutral density filters. The laser beam was linearly polarized along the horizontal direction.

A Fourier space gate was realized by placing the sample at the back focal plane of a 225 mm focal length lens and by placing a variable diameter aperture at the front focal plane of said lens with the center of the aperture at the focus. A 50 mm focal length camera lens placed on the optical axis at a distance of 50 mm from the aperture was used to collect and to collimate the low spatial frequency light filtered by the aperture and directed it to the 128×128 pixels sensing element of an InGaAs NIR area camera (Sensors Unlimited SU 128-1.7 RT). The pixel size was 25 $\mu$m.

A polarization gate was integrated into the above-described apparatus using a first linear polarizer before the sample cell and a second linear polarizer before the camera. The polarization axis of the second polarizer was made to be adjustable to enable the parallel and perpendicular components of the transmitted light to be measured.

To test the apparatus, a normal human breast tissue specimen was used. The specimen was derived from the left breast of a 28-year-old female patient following reduction mammoplasty. It was made available to the present inventors by National Disease Research Interchange under an IRB at City College of New York. The specimen, which had dimensions of approximately 70 mm×50 mm×5 mm, contained fat tissue with. broad strands of firm fibrous tissue. A portion of the specimen measuring approximately 35 mm×14 mm×5 mm and comprising fatty tissue in the middle and fibrous tissue on opposite sides was used as the sample tested by the apparatus.

Two-dimensional shadowgram images of the sample obtained with the apparatus of FIG. 5 using near-infrared light of wavelengths 1225 nm, 1235 mm, 1255 nm, 1285 nm and 1300 nm are shown in the left frames of FIGS. 6(a) through 6(e), respectively. Corresponding spatial intensity distributions of the images integrated over the same horizontal area as highlighted by the white dashed box in FIGS. 6(a) through 6(e) are shown in the frames to the right of the respective images. The fatty region in the middle of the sample appears much darker and more distinct from the fibrous regions on the two sides in the 1225 nm image. The region appears as a deep trough in the corresponding spatial intensity distribution. Optical absorption due to fat is higher at 1225 nm than that at the other four wavelengths displayed in FIGS. 6(b) through 6(e). As the wavelength of the Cr:forsterite laser output was tuned out of the fat absorption band. the contrast between the fatty and fibrous regions in the images decreased. The depth of the trough in the spatial intensity profile also decreased and the region appeared as a crest in the profiles of the images recorded using 1255 nm or longer wavelength light. For wavelengths further removed from the resonance, such as 1300 nm, the adipose region appeared brighter than the fibrous regions. The present inventors believe that this difference is attributable to (a) higher light scattering by adipose tissues compared to fibrous tissues, and (b) the spatial intensity distribution of the incident beam which is not quite flat but has a broad peak; since the adipose tissue was located in the middle of the specimen, it was illuminated by the central part of the beam.

Figure 7:
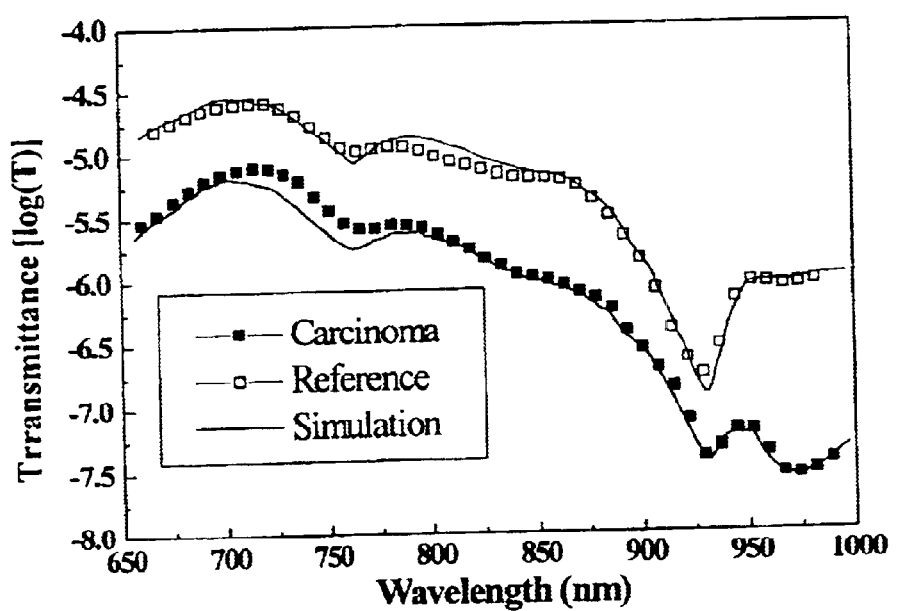
FIG. 7 is a graphic representation of the in vivo optical transmission spectra of cancerous and normal human breast tissues: as a function of wavelength.

The above-discussed experiment clearly demonstrates that a wavelength-dependent difference in spectroscopic properties between two types of tissues can be used to form optical images with a contrast between the two tissues. Similarly, tumors or other lesions inside the human body may be detected using such spectroscopic imaging. The key is the spectroscopic differences between normal and diseased tissues. All of the particular values of key optical, spectroscopic and light-transport parameters as a function of wavelength for different types of tissues and lesions are not known at present, but there is no reason to doubt that such values are certainly capable of being discerned by those of ordinary skill in the art in a routine manner. For example, as seen in FIG. 7, salient differences between the spectra of normal and cancerous breast tissues include (a) the overall lower transmittance of the cancerous breast tissue, and (b) different curve profiles in the 900–1000 nm spectral range that is attributed to an alteration in the water and fat contents of the normal and cancerous breast tissues.

Figure 8:
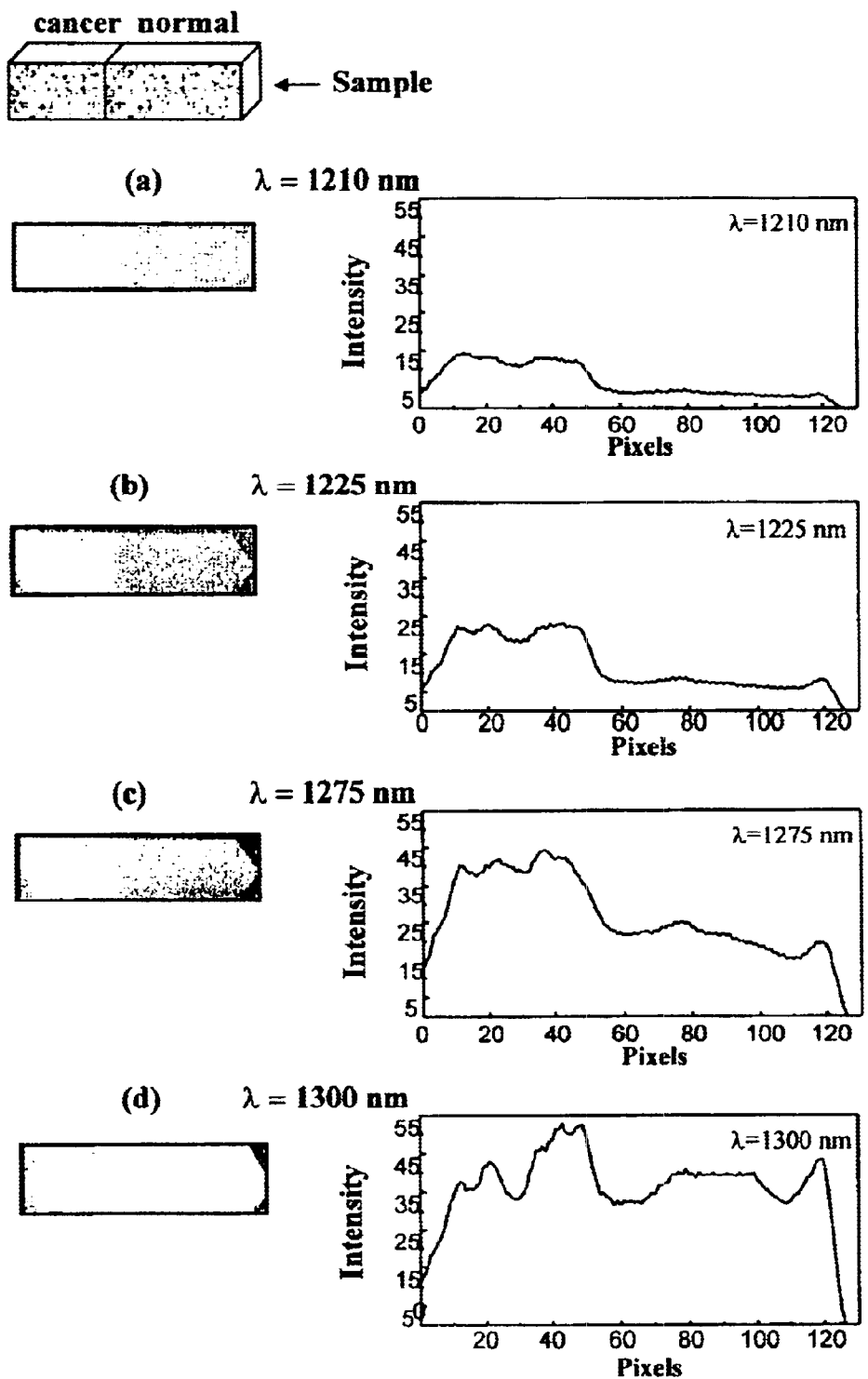
FIG. 8 is a perspective view of a 10 mm×30 mm×5 mm excised human breast tissue specimen comprising normal and cancerous portions.

Using the apparatus of FIG. 5, a 10 mm×30 mm×5 mm breast tissue specimen from a 41 year-old female patient following "right modified radial mastectomy," was tested, the specimen being provided by National Disease Research Interchange under an IRB at City College of New York. A surgical pathology report had identified the tumor as being of the invasive ductal carcinoma, mucinous type. The specimen is shown in FIG. 8, and the results of using the apparatus of FIG. 5 to image the specimen are shown in FIGS. 8(a) through 8(d). The salient feature of the images of FIGS. 8(a) through 8(d) is that the ratio of light intensity transmitted through the cancerous tissue to light intensity transmitted through the normal tissue, henceforth referred to as $R_{CN}$, decreases from 3.0 at 1210 nm to 1.3 at 1300 nm. Similar spectroscopic behavior was observed in tissues from other patients. The differences in these spectroscopic images provide a basis for diagnostic optical imaging of lesions in accessible parts of the human body, and the value of $R_{CN}$ can be used as a parameter to characterize a tissue as normal or cancerous.

Figure 9:
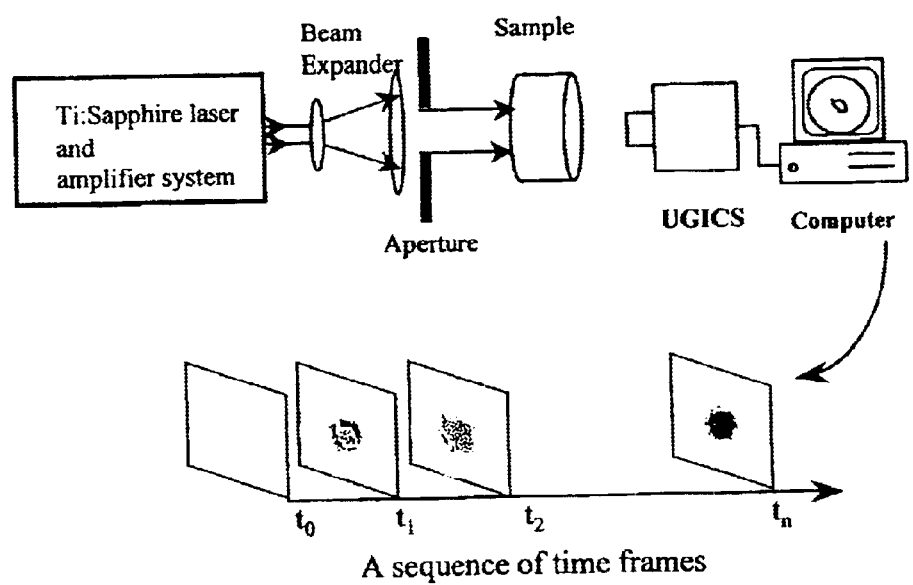
FIG. 9 is a schematic diagram of a second embodiment of an imaging apparatus constructed according to the teachings of the present invention.
Figure 10:
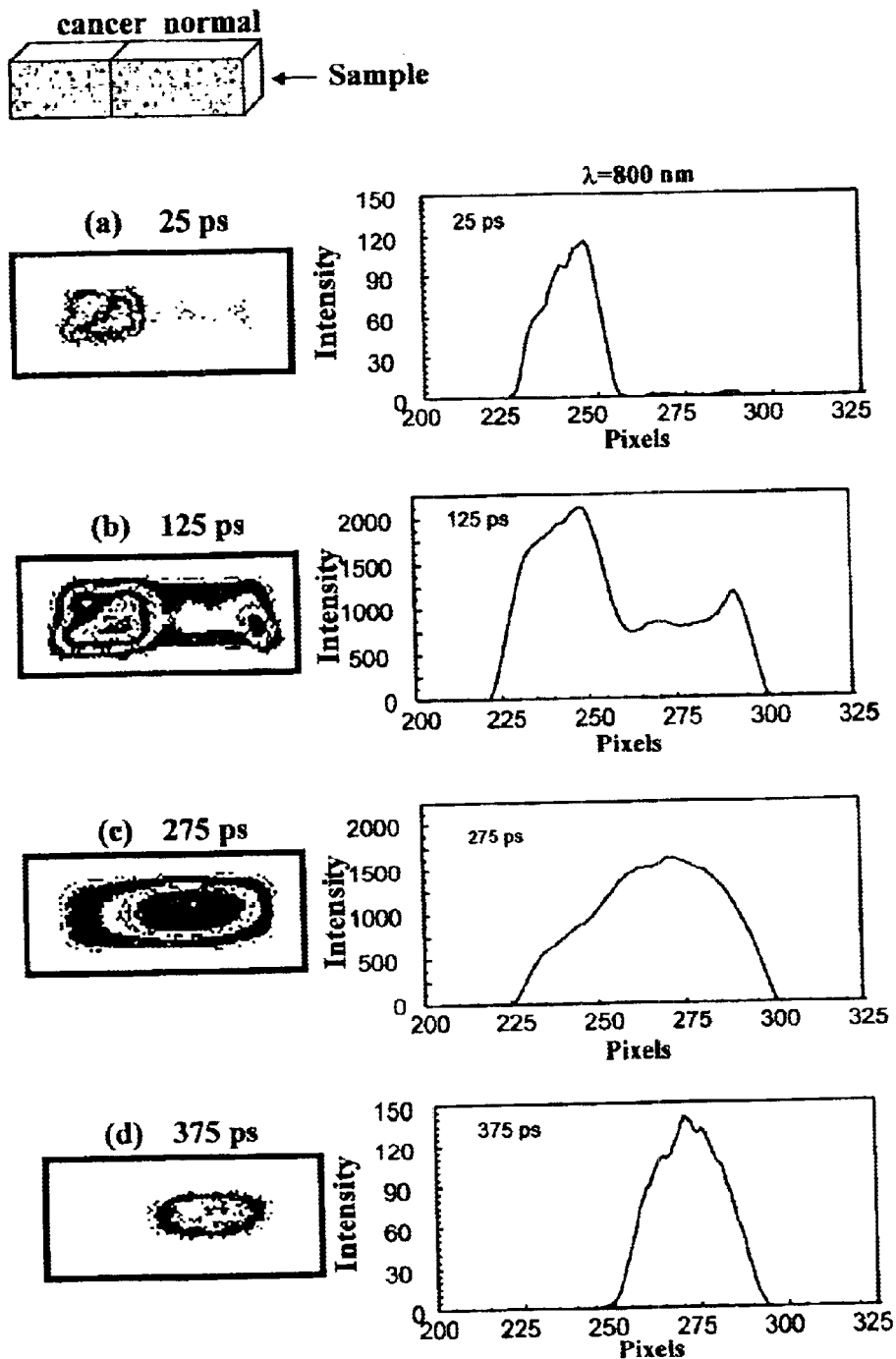
FIGS. 10(a) through 10(d) are time-sliced 2-D transillumination images (left frame) and corresponding spatial profiles of the integrated intensity distribution along the same horizontal area (right frame) of the specimen of FIG. 8 obtained using the apparatus of FIG. 9 with time-gate positions of (a) 25 ps; (b) 125 ps; (c) 275 ps; and (d) 375 ps, respectively.

Referring now to FIG. 9, there is schematically shown an experimental imaging apparatus including an electronic time gate of 80 ps, which was used to obtain a plurality of 2-D time-sliced images. The apparatus used a self-mode-locked Ti:sapphire laser and amplifier system to generate 130 fs duration, 1 kHz repetition rate pulses of 800 nm light. The average beam power used in the experiment was approximately 200 mW. The beam was expanded by a beam expander, and a 3-cm diameter central part of the beam was used to illuminate the sample. Time-sliced imaging was accomplished using an ultrafast gated intensified camera system (UGICS) comprising a compact time-gated image intensifier unit fiber-optically coupled to a charge-coupled device (CCD) camera. The transmitted light from the sample was collected by a camera lens and directed to the image intensifier. The system provided an electronic gate pulse whose full-width-at-half-maximum (FWHM) duration could be adjusted to a minimum of approximately 80 ps. The gate position was capable of being varied in steps of 25 ps over a 20 ns range. The signal recorded by the system at a particular gate position was a convolution of the transmitted light pulse with the gate pulse centered on the gate position. The system was used to obtain a sequence of time-resolved 2-D images (that were 2-D spatial intensity distribution integrated over an 80 ps slice of time) for different gate positions. These time-resolved images are herein referred to as time-sliced images. These time-sliced images were recorded by the CCD camera and displayed and stored on a personal computer. Although the individual images provide a 2-D projection of a 3-D object, a sequence of the images recorded at different times may be used for reconstruction of a 3-D tomographic image.

Time-sliced 2-D shadow images of the 10 mm×30 mm×5 mm breast tissue specimen of FIG. 8 with gate positions at 25 ps, 125 ps, 275 ps, and 375 ps are displayed in the left frames of FIGS. 10(a) through 10(d), respectively. The zero position was taken to be the time of arrival of the light pulse through a 5 mm thick glass cell filled with water. The spatial distribution of transmitted light intensity integrated along a horizontal area covering both the normal and cancerous regions of the tissue sample showing the relative magnitude of light transmitted through the regions is displayed in the corresponding right frames of FIGS. 10(a) through 10(d), respectively. As can be seen, the intensity of light transmitted through the cancerous tissue is much higher in the 25 ps image than that transmitted through the normal tissue. After some time, the ratio of light intensity transmitted through the cancerous tissue to light intensity transmitted through the normal tissue decreased. At much later times, the intensity of light transmitted through the normal region was much higher than that through the cancerous region, as displayed in FIG. 10(d). The distinction between the cancerous and normal regions is highlighted in the 25 ps and the 375 ps images.

The present inventors attribute the aforementioned difference in the relative light transmission between the normal and the cancerous human breast tissues to the higher scattering of light by the normal tissue. Photons transiting the normal region scatter more and, therefore, come out later than photons transiting the cancerous region. This result is consistent with the transport mean free path $l_t$ values of 1 mm for cancerous tissue and 0.8 mm for normal tissue reported in the literature. See Peters et al., "Optical properties of normal and diseased human breast tissues in the visible and near infrared," *Phys. Med. Biol.*, 9:1317–34 (1990). The present inventors have elsewhere shown that, in the 700–1300 nm range, $l_t$ for cancerous tissue has a higher value than that for normal fibrous tissue and that $l_t$ for adipose tissue has a lower value than that for normal fibrous tissue, i.e., $l_{tFAT} < l_{tNORMAL} < l_{tCANCER}$.

As noted above, a series of time-sliced images can be used for 3-D inverse reconstruction, for example, to provide the location of an object inside a scattering medium (e.g., a tumor within a breast). To demonstrate the foregoing, 2-D images of a black-painted aluminum rectangular parallelepiped inside a cylindrical cell containing Intralipid-10% (Kabi Pharmacia Inc., Clayton, N.C.) in water were obtained using the apparatus of FIG. 9, which is described in detail in Cai et al., "Optical tomographic image reconstruction from ultrafast time-sliced transmission measurements," *Appl. Opt.*, 38:4237–46 (1999). Intralipid-10% is a fat emulsion used clinically as a nutrient and in research as a phantom to investigate light propagation in tissues. The concentration of Intralipid-10% for purposes of the present experiment was adjusted to provide a transport mean free path of 2.5 mm and an absorption length of 50 mm at 800 nm. The dimensions of the object were 3 mm×3 mm×10 mm, and the dimensions of the cylindrical cell were 100 mm in diameter and 60 mm in length (comparable to the thickness of an average breast under compression during X-ray mammography). Light was incident on one end face of the cylindrical cell, and the transmitted light was collected from the other end face. The object was placed at an axial distance of 45 mm from the input end face.

A sequence of 2-D spatial intensity patterns recorded in 100 ps intervals over a 5 ns range was obtained using the above apparatus and was used as experimental data for inverse reconstruction. The reconstruction formalism was based on the diffusion approximation of the radiative transport theory for photon migration in a scattering medium. The formulation of the forward problem used a slab geometry in cylindrical coordinates. A Green's function perturbative approach under the Rytov approximation was used to provide a linear inverse algorithm. The forward problem was represented in a matrix form as Y=W X, where Y is a vector represented by a column matrix whose elements are measured changes in the transmitted intensity, X is a vector whose elements are optical parameter (absorption or scattering coefficients) changes due to the presence of the object, and W is the weight function. The vector Y has M elements, determined from experimental data as $Y_i=-\log(I/I_{0i})$, where $I_0$ and $I_{0i}$ are the measured intensities with and without the object, respectively, and $M=(n_t X_r X n_\phi)$ where $n_t$ is the number of time slices and $n_r$ and $n_\phi$ are the numbers of radial and angular sections, respectively, that the detector plane is divided into. X has N elements, $X_j=c\Delta\mu_a(r_j)$, where N is the number of voxels that the sample cell is divided into, and $\Delta\mu_a$ is the absorption coefficient change. W is an M×N matrix that under the assumptions of a cylindrical boundary and a uniform reference medium satisfies the $\phi$-rotation invariance. The cylindrical symmetry enables use of a 2-D matrix inversion with a one-dimensional Fourier transform inversion in the inversion algorithm to achieve speedy 3-D image reconstruction. An L-curve method, such as is disclosed in the herein incorporated by reference Hansen, "Analysis of discrete ill-posed problems by means of the L curve," *SIAM Rev.*, 34:561–80 (1992), was used to choose the regularization parameters needed to obtain a unique solution of the inversion problem.

Figure 11:
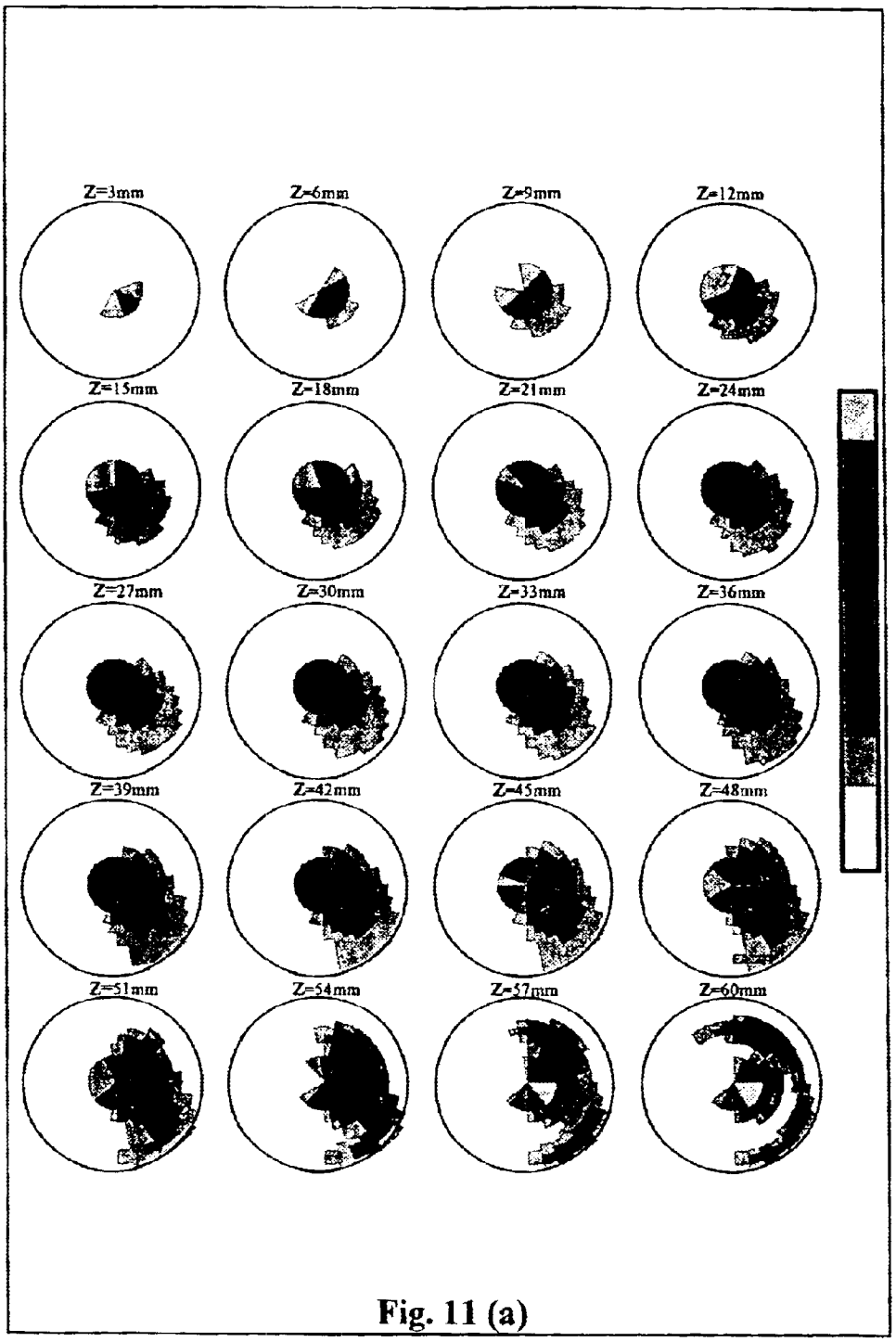
FIGS. 11(a) and 11(b) represent series of inverse reconstructed images of a 3 mm×3 mm×3 mm absorbing object placed inside a 100 mm diameter×60 mm thick cylindrical cell containing a scattering medium comprising Intralipid suspension in water (the transport length and the absorption mean free path of the scattering medium being 2.5 mm and 50 mm, respectively) and transilluminated with 800 nm light along one of the flat end faces of the cylindrical cell (the object being placed 15 mm into the cell from the detector end face) using (a) experimental data; and (b) simulated data, respectively.
Figure 11:
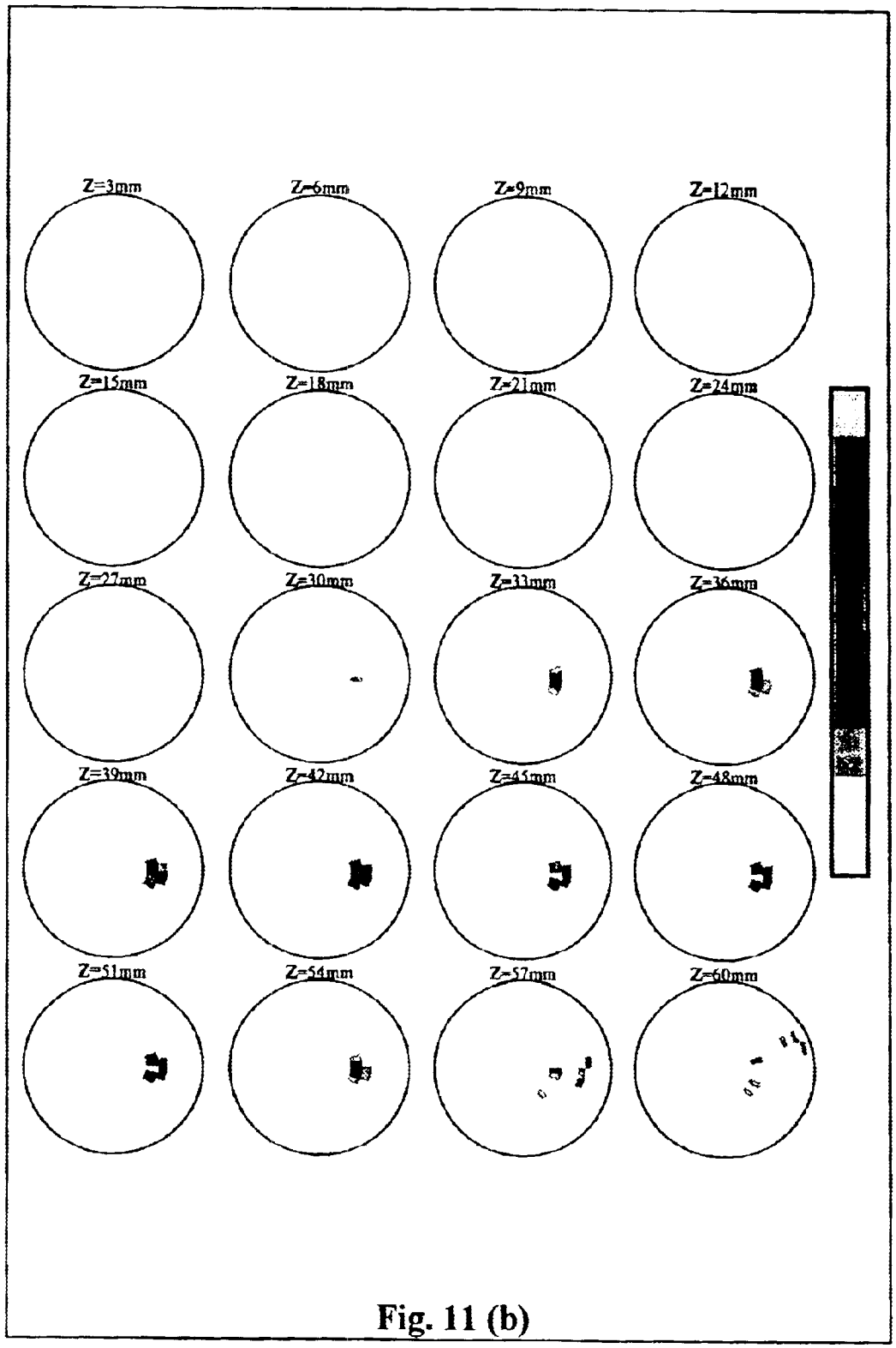

FIG. 11(*a*) shows a 3-D image of the object as a sequence of frames at 3 mm intervals along the axial direction, said image being reconstructed using the above-described experimental data. The lateral portion of the object is reconstructed to be near the cylinder axis in the image map, as one would expect. The axial position estimated to be closer to the detector end of the cell, however, is spread out with a half width of approximately 20 mm along the axial direction. In order to understand the reason for this spreading, an image reconstruction was performed using simulated data with a 5% Gaussian distributed noise, the results being shown in FIG. 11(*b*). As can be seen, the image is localized around the 15$^{th}$ circle, that is, at the axial location of 45 mm from the input end, as expected. Results from simulation indicate that the noise level was higher than 5% in the experimental data, causing the spreading out of the image and deteriorating the resolution along the axial direction. The experimental noise may arise from fluctuations in the energy of the pulses of laser light, jitters in the position and width of the time gate, and CCD dark noise. The noise problem may be improved with better design and control of experimental apparatus, leading to more accurate determination of object location.

Inverse reconstruction imaging using data from a backscattering geometry (which also forms a part of the present invention) is expected to be more resistant to noise than such imaging using data from a transmission geometry.

As can readily be appreciated, the above-described inverse reconstruction imaging technique can also be performed using light at different wavelengths, at least one of which is selectively absorbed (or scattered) by the object. Such a technique could be used to provide simultaneous location and diagnosis of a tumor inside a body part.

Figure 12:
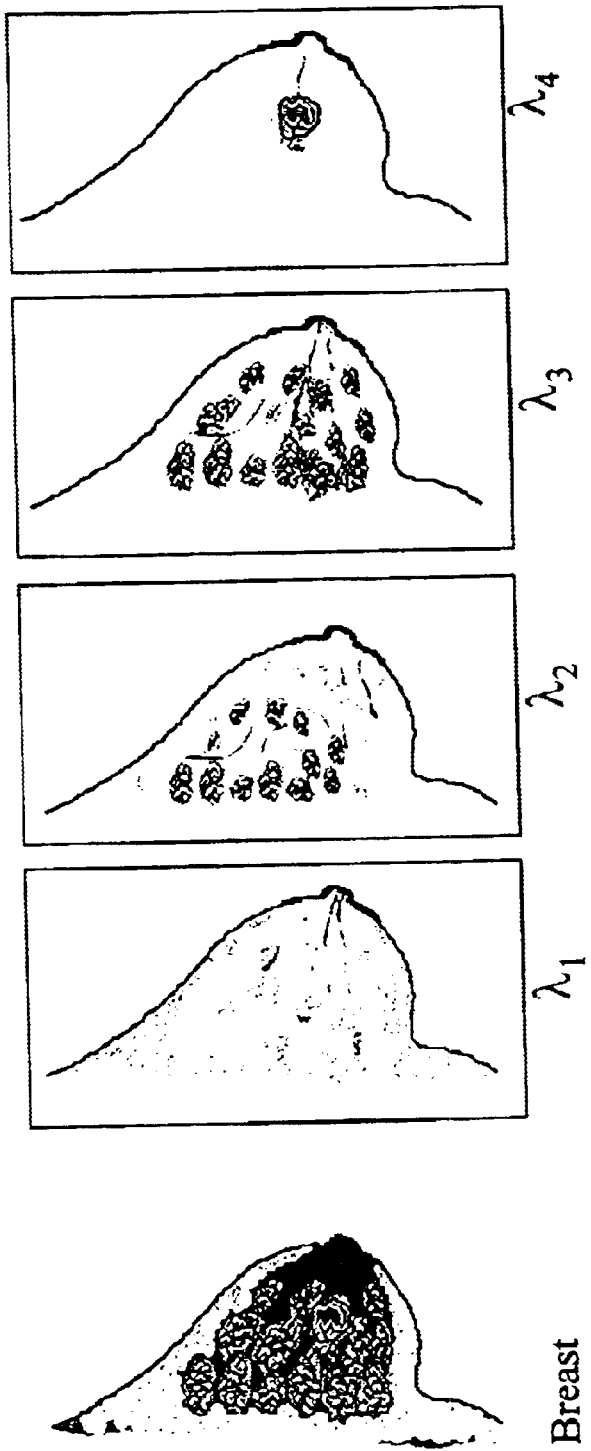
FIG. 12 is a series of schematic diagrams illustrating how different types of breast components may be selectively detected by tuning the illuminating light to wavelengths specific therefor (e.g., $\lambda_1$ could be 965 nm or 1177 nm to detect water, $\lambda_2$ could be 1036 or 1203 nm to detect fat, $\lambda_n$ could be 760 nm to detect Hb, and so on).

The scope and potential of 3-D inverse image reconstruction using time-sliced 2-D images recorded with light of different wavelengths are shown schematically in FIG. 12. A 3-D image reconstructed from 2-D time-sliced images recorded with light of $\lambda_1$ that resonates with an optical property of a component of the turbid medium (e.g., absorption of 1203 nm light by adipose tissues in the breast) can be used to provide a 3-D map of that component (e.g., adipose tissue). A second wavelength $\lambda_2$ (e.g., in the range of 670–790 nm) can be used to provide a 3-D map of the second component (deoxyhemoglobin). A third wavelength $\lambda_3$ (e.g., in the range of 810–900 nm) can be used to provide a 3-D map of the third component (oxyhemoglobin). Necrotic regions can be highlighted by a difference image obtained by subtracting the hemoglobin image tree from the -deoxyhemoglobin image tree. Similarly, by identifying a particular wavelength as being resonant with a certain type of breast cancer, one can use that wavelength to produce a 3-D map of the location and proliferation of that type of cancer in the breast.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method of imaging an object in medium, wherein said object is a tumor and said turbid medium is a tissue, said method comprising the steps of:

(a) illuminating at least a portion of the turbid medium with substantially monochromatic light of a first wavelength, said illuminated portion of the turbid medium comprising the object, said first wavelength being selected from the group consisting of a wavelength in the range of 940–1010 nm, a wavelength in the range of 1120–1240 nm, and a wavelength in the range of 1400–1500 nm;

(b) wherein each of the turbid medium and the object has a resonance wavelength for an optical property, wherein the respective resonance wavelengths for the turbid medium and the object are different for said optical property and wherein said substantially monochromatic light of said first wavelength is equal in wavelength to the resonance wavelength for said optical property of one of the turbid medium and the object;

(c) using at least a portion of the light emergent from the turbid medium to form an image of the object in the turbid medium.

2. The method as claimed in claim 1 wherein the light emergent from the turbid medium comprises a ballistic component, a snake component and a diffuse component and wherein said using step comprises preferentially selecting from the emergent light the ballistic and snake components thereof, detecting the preferentially selected light, and forming an image of the object with the detected preferentially selected light.

3. The method as claimed in claim 2 wherein said substantially monochromatic light of said first wavelength is laser light obtained from a laser selected from the group consisting of $Cr^{+4}$:forsterite, Cr:YAG, $Cr:Ca_2GeO_4$, Ti:sapphire, alexandrite, $Cr^{+3}$:LiCaAlF$_6$, $Cr^{+3}$:LiSrAlF$_6$, Nd:YAG, gas, dye, solid-state, color center, and semiconductor lasers.

4. The method as claimed in claim 2 wherein said substantially monochromatic light of said first wavelength is a pulse of light.

5. The method as claimed in claim 2 wherein said substantially monochromatic light of said first wavelength is continuous light.

6. The method as claimed in claim 2 wherein said preferential selecting step comprises gating the emergent light with a gate selected from the group consisting of a space gate, a Fourier gate, a time gate, a time/space gate, a polarization gate, a confocal gate a nonlinear optical gate, a coherence gate and a combination thereof.

7. The method as claimed in claim 6 wherein said gate is a time gate selected from the group consisting of an electronic time gate, an optical Kerr gate, a second harmonic generation cross correlation gate, a four-wave mixing gate, an upconversion gate and a combination thereof.

8. The method as claimed in claim 2 wherein said detecting step comprises detecting the preferentially selected light using a light detector selected from the group consisting of a CCD camera, a near-infrared area camera, a one-dimensional array of detectors, photodiodes, photomultiplier tubes, and a streak camera.

9. The method as claimed in claim 1 wherein said illuminating and detecting steps are performed in a backscattering geometry.

10. A method of imaging an object in a turbid medium, wherein said object is a tumor and said turbid medium is a tissue, said method comprising the steps of:
 (a) illuminating at least a portion of the turbid medium with substantially monochromatic light of a first wavelength, said illuminated portion of the turbid medium comprising the object, wherein said substantially monochromatic light of said first wavelength is amplitude-modulated light and wherein the light emergent from the turbid medium comprises a ballistic component, a snake component and a diffuse component;
 (b) wherein each of the turbid medium and the object has a resonance wavelength for an optical property, wherein the respective resonance wavelengths for the turbid medium and the object are different for said optical property and wherein said substantially monochromatic light of said first wavelength is equal in wavelength to the resonance wavelength for said optical property of one of the turbid medium and the object;
 (c) using at least a portion of the light emergent from the turbid medium to form an image of the object in the turbid medium, wherein said using step comprises preferentially selecting from the emergent light the ballistic and snake components thereof, detecting the preferentially selected light, and forming an image of the object with the detected preferentially selected light.

11. A method of imaging an object in a turbid medium, wherein the turbid medium is a human body part, said method comprising the steps of:
 (a) illuminating at least a portion of the turbid medium with substantially monochromatic light of a first wavelength, said illuminated portion of the turbid medium comprising the object, wherein the light emergent from the turbid medium comprises a ballistic component, a snake component and a diffuse component, said first wavelength being selected from the group consisting of a wavelength in the range of 940–1010 nm, a wavelength in the range of 1120–1240 nm, and a wavelength in the range of 1400–1500 nm;
 (b) wherein each of the turbid medium and the object has a resonance wavelength for an optical property, wherein the respective resonance wavelengths for the turbid medium and the object are different for said optical property and wherein said substantially monochromatic light of said first wavelength is equal in wavelength to the resonance wavelength for said optical property of one of the turbid medium and the object;
 (c) using at least a portion of the light emergent from the turbid medium to form an image of the object in the turbid medium; and
 (d) wherein said using step comprises preferentially selecting from the emergent light the ballistic and snake components thereof, detecting the preferentially selected light, and forming an image of the object with the detected preferentially selected light.

12. A method of imaging an object in a turbid medium, wherein the turbid medium is a human body part selected from the group consisting of the breast, the brain, the bladder, the gastrointestinal tract, the prostate, the cervix, the colon, and the eye, said method comprising the steps of:
 (a) illuminating at least a portion of the turbid medium with substantially monochromatic light of a first wavelength, said illuminated portion of the turbid medium comprising the object, wherein the light emergent from the turbid medium comprises a ballistic component, a snake component and a diffuse component, said first wavelength being selected from the group consisting of a wavelength in the range of 940–1010 nm a wavelength in the range of 1120–1240 nm and a wavelength in the range of 1400–1500 nm;
 (b) wherein each of the turbid medium and the object has a resonance wavelength for an optical property, wherein the respective resonance wavelengths for the turbid medium and the object are different for said optical property and wherein said substantially monochromatic light of said first wavelength is equal in wavelength to the resonance wavelength for said optical property of one of the turbid medium and the object;
 (c) using at least a portion of the light emergent from the turbid medium to form an image of the object in the turbid medium; and
 (d) wherein said using step comprises preferentially selecting from the emergent light the ballistic and snake components thereof, detecting the preferentially selected light, and forming an image of the object with the detected preferentially selected light.

13. A method of imaging an object in a turbid medium, wherein the turbid medium is the breast, said method comprising the steps of:
 (a) illuminating at least a portion of the turbid medium with substantially monochromatic light of a first wavelength, said illuminated portion of the turbid medium comprising the object, wherein the light emergent from the turbid medium comprises a ballistic component, a snake component and a diffuse component, said first wavelength being selected from the group consisting of a wavelength in the range of 940–1010 nm, a wavelength in the range of 1120–1240 nm, and a wavelength in the range of 1400–1500 nm;

(b) wherein each of the turbid medium and the object has a resonance wavelength for an optical property, wherein the respective resonance wavelengths for the turbid medium and the object are different for said optical property and wherein said substantially monochromatic light of said first wavelength is equal in wavelength to the resonance wavelength for said optical property of one of the turbid medium and the object;

(c) using at least a portion of the light emergent from the turbid medium to form an image of the object in the turbid medium; and (d) wherein said using step comprises preferentially selecting from the emergent light the ballistic and snake components thereof, detecting the preferentially selected light, and forming an image of the object with the detected preferentially selected light.

14. A method of imaging an object in a turbid medium, said method comprising the steps of:

(a) illuminating at least a portion of the turbid medium with substantially monochromatic light of a first wavelength, said illuminated portion of the turbid medium comprising the object;

(b) wherein each of the turbid medium and the object has a resonance wavelength for an optical property, wherein the respective resonance wavelengths for the turbid medium and the object are different, wherein said substantially monochromatic light of said first wavelength is equal in wavelength to the resonance wavelength for said optical property of one of the turbid medium and the object and wherein said first wavelength is selected from the group consisting of a wavelength in the range of 940–1010 nm, a wavelength in the range of 1120–1240 nm, and a wavelength in the range of 1400–1500 nm;

(c) detecting at least a portion of the light emergent from the turbid medium in response to illumination with said substantially monochromatic light of said first wavelength;

(d) illuminating at least a portion of the turbid medium with substantially monochromatic light of a second wavelength, said illuminated portion of the turbid medium comprising the object;

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength; and (g) using the light detected in step (c) to form a resonant image and that detected in step (f) to form a non-resonant image of the object in the turbid medium.

15. The method as claimed in claim 14 wherein the light emergent from the turbid medium following illumination with each of said substantially monochromatic light of said first wavelength and said substantially monochromatic light of said second wavelength comprises a ballistic component, a snake component and a diffuse component and wherein said method further comprises, after step (a) and before step (c), the step of preferentially selecting from the emergent light the ballistic and snake components thereof and also comprises, after step (d) and before step (f), the step of preferentially selecting from the emergent light the ballistic and snake components thereof, and wherein each of said detecting steps comprises detecting the preferentially selected light.

16. The method as claimed in claim 15 wherein said using step comprises using a difference of the resonant and non-resonant images to form an image of the object in the turbid medium.

17. The method as claimed in claim 14 wherein step (a) is performed using a light source whose wavelength output is variable and wherein step (d) is also performed using said light source.

18. The method as claimed in claim 14 wherein the light emergent from the turbid medium following illumination with each of said substantially monochromatic light of said first wavelength and said substantially monochromatic light of said second wavelength comprises a ballistic component, a snake component and a diffuse component, wherein each of said detecting steps comprises determining the intensity of the diffuse component at a plurality of points in time and wherein said using step comprises using said pluralities of intensity determinations and a mathematical inversion algorithm to form an image of the object in the turbid medium.

19. The method as claimed in claim 18 wherein the image is a 2-D image.

20. The method as claimed in claim 18 wherein said illuminating and detecting steps are performed in a back-scattering geometry.

21. A method of imaging an object in a turbid medium, said method comprising the steps of:

(a) illuminating at least a portion of the turbid medium with substantially monochromatic light of a first wavelength, said illuminated portion of the turbid medium comprising the object, wherein the light emergent from the turbid medium following illumination with said substantially monochromatic light of said first wavelength comprises a ballistic component, a snake component and a diffuse component;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) preferentially selecting from the emergent light the ballistic and snake components thereof;

(d) detecting at least a portion of the light emergent from the turbid medium in response to illumination with said substantially monochromatic light of said first wavelength;

(e) illuminating at least a portion of the turbid medium with substantially monochromatic light of a second wavelength, said illuminated portion of the turbid medium comprising the object, wherein the light emergent from the turbid medium following illumination with said substantially monochromatic light of said second wavelength comprises a ballistic component, a snake component and a diffuse component:

(f) preferentially selecting from the emergent light the ballistic and snake components thereof;

(g) wherein said substantially monochromatic light of said second wavelength is not equal in wavelength to the resonance wavelength for said optical property of either the turbid medium or the object;

(h) detecting at least a portion of the light emergent from the turbid medium in response to illumination with said substantially monochromatic light of said second wavelength; and (i) using the light detected in step (d) to form a resonant image and that detected in step (h) to form a non-resonant image of the object in the turbid medium, wherein said using step comprises using a ratio of the resonant and non-resonant images to form an image of the object in the turbid medium.

22. A method of imaging an object in a turbid medium, wherein the turbid medium is a human body part, said method comprising the steps of:

(a) illuminating at least a portion of the turbid medium with substantially monochromatic light of a first wavelength, said illuminated portion of the turbid medium comprising the object;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) detecting at least a portion of the light emergent from the turbid medium in response to illumination with said substantially monochromatic light of said first wavelength;

(d) illuminating at least a portion of the turbid medium with substantially monochromatic light of a second wavelength, said illuminated portion of the turbid medium comprising the object;

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength; and (g) using the light detected in step (c) to form a resonant image and that detected in step (f) to form a non-resonant image of the object in the turbid medium.

23. A method of imaging an object in a turbid medium, wherein the image is a 3-D image, said method comprising the steps of:

(a) illuminating at least a portion of the turbid medium with substantially monochromatic light of a first wavelength, said illuminated portion of the turbid medium comprising the object, wherein the light emergent from the turbid medium following illumination with said substantially monochromatic light of said first wavelength comprises a ballistic component, a snake component and a diffuse component;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) detecting at least a portion of the light emergent from the turbid medium in response to illumination with said substantially monochromatic light of said first wavelength, wherein said detecting step comprises determining the intensity of the diffuse component at a plurality of points in time;

(d) illuminating at least a portion of the turbid medium with substantially monochromatic light of a second wavelength, said illuminated portion of the turbid medium comprising the object, wherein the light emergent from the turbid medium following illumination with said substantially monochromatic light of said second wavelength comprises a ballistic component, a snake component and a diffuse component;

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength, wherein said detecting step comprises determining the intensity of the diffuse component at a plurality of points in time; and (g) using the light detected in step (c) to form a resonant image and that detected in step (f) to form a non-resonant image of the object in the turbid medium, wherein said using step comprises using said pluralities of intensity determinations and a mathematical inversion algorithm to form a 3-D image of the object in the turbid medium.

24. A method of imaging an object in a turbid medium, said method comprising the steps of:

(a) illuminating at least a portion of the turbid medium with substantially monochromatic light of a first wavelength, said illuminated portion of the turbid medium comprising the object, wherein the light emergent from the turbid medium following illumination with said substantially monochromatic light of said first wavelength comprises a ballistic component, a snake component and a diffuse component;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) detecting at least a portion of the light emergent from the turbid medium in response to illumination with said substantially monochromatic light of said first wavelength, wherein said detecting step comprises determining the intensity of the diffuse component at a plurality of points in time;

(d) illuminating at least a portion of the turbid medium with substantially monochromatic light of a second wavelength, said illuminated portion of the turbid medium comprising the object, wherein the light emergent from the turbid medium following illumination with said substantially monochromatic light of said second wavelength comprises a ballistic component, a snake component and a diffuse component;

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength, wherein said detecting step comprises determining the intensity of the diffuse component at a plurality of points in time; and (g) using the light detected in step (c) to form a resonant image and that detected in step (f) to form a non-resonant image of the object in the turbid medium, wherein said using step comprises using said pluralities of intensity determinations and a mathematical inversion algorithm to form an image of the object in the turbid medium;

(h) wherein said illuminating and detecting steps are performed in a transmission geometry.

25. A method of imaging an object in a turbid medium, said method comprising the steps of:

(a) illuminating at least a portion of the turbid medium with substantially monochromatic light of a first wavelength, said illuminated portion of the turbid medium comprising the object, wherein the light emergent from the turbid medium following illumination with said substantially monochromatic light of said first wavelength comprises a ballistic component, a snake component and a diffuse component;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) detecting at least a portion of the light emergent from the turbid medium in response to illumination with said substantially monochromatic light of said first wavelength, wherein said detecting step comprises determining the intensity of the diffuse component at a plurality of points in time and at a plurality of locations around the turbid medium;

(d) illuminating at least a portion of the turbid medium with substantially monochromatic light of a second wavelength, said illuminated portion of the turbid medium comprising the object, wherein the light emergent from the turbid medium following illumination with said substantially monochromatic light of said second wavelength comprises a ballistic component, a snake component and a diffuse component;

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength, wherein said detecting step comprises determining the intensity of the diffuse component at a plurality of points in time and at a plurality of locations around the turbid medium; and (g) using the light detected in step (c) to form a resonant image and that detected in step (f) to form a non-resonant image of the object in the turbid medium, wherein said using step comprises using said pluralities of intensity determinations and a mathematical inversion algorithm to form an image of the object in the turbid medium.

26. A method of imaging an object in a turbid medium, wherein the turbid medium is a human body part, said method comprising the steps of:

(a) illuminating at least a portion of the turbid medium with substantially monochromatic light of a first wavelength, said illuminated portion of the turbid medium comprising the object;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) detecting at least a portion of the light emergent from the turbid medium in response to illumination with said substantially monochromatic light of said first wavelength;

(d) illuminating at least a portion of the turbid medium with substantially monochromatic light of a second wavelength, said illuminated portion of the turbid medium comprising the object;

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength; and (g) using the light detected in step (c) to form a resonant image and that detected in step (f) to form a non-resonant image of the object in the turbid medium;

(h) wherein the light emergent from the turbid medium following illumination with each of said substantially monochromatic light of said first wavelength and said substantially monochromatic light of said second wavelength comprises a ballistic component, a snake component and a diffuse component, wherein each of said detecting steps comprises determining the intensity of the diffuse component at a plurality of points in time and wherein said using step comprises using said pluralities of intensity determinations and a mathematical inversion algorithm to form an image of the object in the turbid medium.

27. A method of imaging an object in a turbid medium, said method comprising the steps of:

(a) illuminating at least a portion of the turbid medium with substantially monochromatic light of a first wavelength, said illuminated portion of the turbid medium comprising the object;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) detecting at least a portion of the light emergent from the turbid medium in response to illumination with said substantially monochromatic light of said first wavelength;

(d) illuminating at least a portion of the turbid medium with substantially monochromatic light of a second wavelength, said illuminated portion of the turbid medium comprising the object;

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength; and (g) using the light detected in step (c) to form a resonant image and that detected in step (f) to form a non-resonant image of the object in the turbid medium;

(h) wherein the turbid medium is a human breast, wherein one and only one of said first wavelength and said second wavelength is a wavelength selected from the group consisting of 950–980 nm and 1150–1350 nm, wherein the light emergent from the turbid medium following illumination with each of said substantially monochromatic light of said first wavelength and said substantially monochromatic light of said second wavelength comprises a ballistic component, a snake component and a diffuse component, wherein each of said detecting steps comprises determining the intensity of the diffuse component at a plurality of points in time and wherein said using step comprises using said pluralities of intensity determinations and a mathematical inversion algorithm to form an image of the object in the turbid medium.

28. A method of imaging an object in a turbid medium, said method comprising the steps of:

(a) illuminating at least a portion of the turbid medium with substantially monochromatic light of a first wavelength, said illuminated portion of the turbid medium comprising the object, wherein the light emergent from the turbid medium following illumination with said substantially monochromatic light of said first wavelength comprises a ballistic component, a snake component and a diffuse component;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) detecting at least a portion of the light emergent from the turbid medium in response to illumination with said substantially monochromatic light of said first wavelength, wherein said detecting step comprises determining the intensity of the diffuse component at a plurality of points in time, wherein said determining step comprises obtaining a sequence of 2-D time-sliced images using different temporal slices of the transmitted light using the ballistic, snake and diffuse photons, said different temporal slices being obtained by positioning the time gate at different points in time;

(d) illuminating at least a portion of the turbid medium with substantially monochromatic light of a second wavelength, said illuminated portion of the turbid medium comprising the object, wherein the light emergent from the turbid medium following illumination with said substantially monochromatic light of said second wavelength comprises a ballistic component, a snake component and a diffuse component;

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength, wherein said detecting step comprises determining the intensity of the diffuse component at a plurality of points in time, wherein said determining step comprises obtaining a sequence of 2-D time-sliced images using different temporal slices of the transmitted light using the ballistic, snake and diffuse photons, said different temporal slices being obtained by positioning the time gate at different points in time; and (g) using the light detected in step (c) to form a resonant image and that detected in step (f) to form a non-resonant image of the object in the turbid medium, wherein said using step comprises using said pluralities of intensity determinations and a mathematical inversion algorithm to form an image of the object in the turbid medium.

29. The method as claimed in claim 28 wherein the reconstructed image is a 3-D image.

30. The method as claimed in claim 29 wherein the 3-D images are reconstructed using light of fingerprint wavelengths that are resonant with certain optical properties of the object enabling construction of a 3-D map of the said optical property, such as use of light around 1200 nm to obtain the adipose tissue distribution in the breast or an appropriate wavelength to obtain the proliferation of certain cancer in the breast.

31. A method of imaging an object in a turbid medium, said method comprising the steps of:

(a) illuminating at least a portion of the turbid medium with substantially monochromatic light of a first wavelength, said illuminated portion of the turbid medium comprising the object, wherein the light emergent from the turbid medium following illumination with said substantially monochromatic light of said first wavelength comprises a ballistic component, a snake component and a diffuse component;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) detecting at least a portion of the light emergent from the turbid medium in response to illumination with said substantially monochromatic light of said first wavelength, wherein said detecting step comprises determining the intensity of the diffuse component at a plurality of points in time, wherein said determining step comprises obtaining a sequence of 2-D time-sliced images using different temporal slices of the back-propagating light including the ballistic, snake and diffuse photons, said different temporal slices being obtained by positioning the gate at different points in time;

(d) illuminating at least a portion of the turbid medium with substantially monochromatic light of a second wavelength, said illuminated portion of the turbid medium comprising the object, wherein the light emergent from the turbid medium following illumination with said substantially monochromatic light of said second wavelength comprises a ballistic component, a snake component and a diffuse component;

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength, wherein said detecting step comprises determining the intensity of the diffuse component at a plurality of points in time wherein said determining step comprises obtaining a sequence of 2-D time-sliced images using different temporal slices of the back-propagating light including the ballistic, snake and diffuse photons, said different temporal slices being obtained by positioning the gate at different points in time; and (p) using the light detected in step (c) to form a resonant image and that detected in step (f) to form a non-resonant image of the object in the turbid medium wherein said using step comprises using said pluralities of intensity determinations and a mathematical inversion algorithm to form an image of the object in the turbid medium.

32. The method as claimed in claim 31 wherein the reconstructed image is a 3-D image.

33. The method as claimed in claim 32 wherein the 3-D images are reconstructed using light of fingerprint wavelengths that are resonant with certain optical properties of the object enabling construction of a 3-D map of said optical property, such as use of 1200 nm light to obtain the adipose tissue distribution in the breast, or an appropriate wavelength to obtain the proliferation of certain cancer in the breast.

34. The method as claimed in claim 33 wherein 3-D maps are obtained using a resonant and a non-resonant wavelength, and a ratio of the two is used to enhance image quality and contrast.

35. The method as claimed in claim 33 wherein 3-D maps are obtained using a resonant and a non-resonant wavelength, and a difference of the two is used to enhance image quality and contast.

36. The method as claimed in claim 35 wherein the fingerprint wavelength is in the 670–790 nm range, highlighting the deoxyhemoglobin distribution.

37. The method as claimed in claim 35 wherein the fingerprint wavelength is in the 810–900 nm range, highlighting the oxyhemoglobin distribution.

38. A method of imaging an object in a turbid medium, wherein the turbid medium is the prostate, said method comprising the steps of:

(a) illuminating at least a portion of the turbid medium with substantially monochromatic light of a first wavelength, said illuminated portion of the turbid medium comprising the object, wherein the light emergent from the turbid medium following illumination with said substantially monochromatic light of said first wavelength comprises a ballistic component, a snake component and a diffuse component;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) detecting at least a portion of the light emergent from the turbid medium in response to illumination with said substantially monochromatic light of said first wavelength;

(d) illuminating at least a portion of the turbid medium with substantially monochromatic light of a second wavelength, said illuminated portion of the turbid medium comprising the object wherein the light emergent from the turbid medium following illumination with said substantially monochromatic light of said second wavelength comprises a ballistic component, a snake component and a diffuse component;

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength; and (g) using the light detected in step (c) to form a resonant image and that detected in step (f) to form a non-resonant image of the object in the turbid medium;

(h) wherein each of said detecting steps comprises determining the intensity of the diffuse component at a plurality of points in time by obtaining a sequence of 2-D time-sliced images using different temporal slices of the back-propagating light including the ballistic, snake and diffuse photons, said different temporal slices being obtained by positioning the gate at different points in time and wherein said using step comprises using said pluralities of intensity determinations and a mathematical inversion algorithm to form an image of the object in the turbid medium, said image being a 3-D image, said 3-D image being reconstructed using a difference of wavelengths that are resonant and non-resonant with certain optical properties of the object enabling construction of a 3-D map of said optical property.

39. A method of imaging an object in a turbid medium, said method comprising the steps of:

(a) illuminating at least a portion of the turbid medium with substantially monochromatic light of a first wavelength, said illuminated portion of the turbid medium comprising the object, wherein said first wavelength is in the 670–790 nm range;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) detecting at least a portion of the light emergent from the turbid medium in response to illumination with said substantially monochromatic light of said first wavelength;

(d) illuminating at least a portion of the turbid medium with substantially monochromatic light of a second wavelength said illuminated portion of the turbid medium comprising the object, wherein said second wavelength is 800 nm;

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength; and (g) using the light detected in step (c) to form a resonant image and that detected in step (f) to form a non-resonant image of the object in the turbid medium, and wherein the difference image highlights the deoxyhemoglobin distribution.

40. A method of imaging an object in a turbid medium, said method comprising the steps of:

(a) illuminating at least a portion of the turbid medium with substantially monochromatic light of a first wavelength, said illuminated portion of the turbid medium comprising the object, wherein said first wavelength is in the 810–900 nm range;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) detecting at least a portion of the light emergent from the turbid medium in response to illumination with said substantially monochromatic light of said first wavelength;

(d) illuminating at least a portion of the turbid medium with substantially monochromatic light of a second wavelength said illuminated portion of the turbid medium comprising the object, wherein said second wavelength is 800 nm:

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength; and (g) using the light detected in step (c) to form a resonant image and that detected in step (f) to form a non-resonant image of the object in the turbid medium, and wherein the difference image highlights the oxyhemoglobin distribution.

41. A method of imaging an object in a turbid medium, said method comprising the steps of:

(a) illuminating at least a portion of the turbid medium with substantially monochromatic light of a first wavelength, said illuminated portion of the turbid medium comprising the object;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) detecting at least a portion of the light emergent from the turbid medium in response to illumination with said substantially monochromatic light of said first wavelength;

(d) illuminating at least a portion of the turbid medium with substantially monochromatic light of a second wavelength, said illuminated portion of the turbid medium comprising the object;

(e) wherein said substantially monochromatic light of said second wavelength is not equal in wavelength to the resonance wavelength for said optical property of either the turbid medium or the object;

(f) detecting at least a portion of the light emergent from the turbid medium in response to illumination with said substantially monochromatic light of said second wavelength; and (g) using the light detected in step (c) to form a resonant image and that detected in step (f) to form a non-resonant image of the object in the turbid medium;

(h) wherein said first wavelength is in the 940–1010 nm range or in the 1400–1500 nm range, wherein said second wavelength is outside the two ranges, and wherein the difference image highlights the water distribution and thus enables detection of lesions that involve changes in the water content of the tissue.

42. An apparatus for imaging an object in a turbid medium, said apparatus comprising:

(a) first illuminating means for illuminating at least a portion of the turbid medium with substantially monochromatic light of a first wavelength, said illuminated portion of the turbid medium comprising the object, wherein said first wavelength is selected from the group consisting of a wavelength in the range of 940–1010 nm, a wavelength in the range of 1120–1240 nm and a wavelength in the range of 1400–1500 nm;

(b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;

(c) second illuminating means for illuminating at least a portion of the turbid medium with substantially monochromatic light of a second wavelength, said illuminated portion of the turbid medium comprising the object;

(d) wherein said substantially monochromatic light of said second wavelength is not equal in wavelength to the resonance wavelength for said optical property of either the turbid medium or the object;

(e) means for detecting at least a portion of the light emergent from the turbid medium following illumination by said first illuminating means and following illumination by said second illuminating means; and (f) means for using the light detected by said detecting means to form an image of the object in the turbid medium.

43. The apparatus as claimed in claim 42 wherein the light emergent from the turbid medium following illumination with each of said substantially monochromatic light of said first wavelength and said substantially monochromatic light of said second wavelength comprises a ballistic component, a snake component and a diffuse component and wherein said apparatus further comprises means for preferentially selecting from the emergent light for transmission to said detecting means the ballistic and snake components of the emergent light.

44. An apparatus for imaging an object in a turbid medium, said apparatus comprising:
- (a) first illuminating means for illuminating at least a portion of the turbid medium with substantially monochromatic light of a first wavelength said illuminated portion of the turbid medium comprising the object wherein the light emergent from the turbid medium following illumination with said substantially monochromatic light of said first wavelength comprises a ballistic component, a snake component and a diffuse component;
- (b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;
- (c) second illuminating means for illuminating at least a portion of the turbid medium with substantially monochromatic light of a second wavelength, said illuminated portion of the turbid medium comprising the object, wherein the light emergent from the turbid medium following illumination with said substantially monochromatic light of said second wavelength comprises a ballistic component, a snake component and a diffuse component;
- (d) wherein said substantially monochromatic light of said second wavelength is not equal in wavelength to the resonance wavelength for said optical property of either the turbid medium or the object;
- (e) means for detecting at least a portion of the light emergent from the turbid medium following illumination by said first illuminating means and following illumination by said second illuminating means, wherein said detecting means comprises means for determining the intensity of the diffuse component at a plurality of points in time; and
- (f) means for using the light detected by said detecting means to form an image of the object in the turbid medium, wherein said using means comprises means for using said pluralities of intensity determinations and a mathematical inversion algorithm to form an image of the object in the turbid medium.

45. A method of imaging an object in a turbid medium, said method comprising the steps of:
- (a) illuminating at least a portion of the turbid medium with substantially monochromatic light of a first wavelength, said illuminated portion of the turbid medium comprising the object, wherein said first wavelength is selected from the group consisting of a wavelength in the range of 940–1010 nm a wavelength in the range of 1120–1240 nm and a wavelength in the range of 1400–1500 nm;
- (b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;
- (c) detecting at least a portion of the light emergent from the turbid medium in response to illumination with said substantially monochromatic light of said first wavelength;
- (d) illuminating at least a portion of the turbid medium with substantially monochromatic light of a second wavelength, said illuminated portion of the turbid medium comprising the object;
- (e) wherein said substantially monochromatic light of said second wavelength is not equal in wavelength to the resonance wavelength for said optical property of either the turbid medium or the object;
- (f) detecting at least a portion of the light emergent from the turbid medium in response to illumination with said substantially monochromatic light of said second wavelength; and
- (g) using the light detected in steps (c) and (f) to form an image of the object in the turbid medium.

46. The method as claimed in claim 45 wherein the light emergent from the turbid medium following illumination with each of said substantially monochromatic light of said first wavelength and said substantially monochromatic light of said second wavelength comprises a ballistic component, a snake component and a diffuse component and wherein said method further comprises, after step (a) and before step (c), the step of preferentially selecting from the emergent light the ballistic and snake components thereof and also comprises, after step (d) and before step (f), the step of preferentially selecting from the emergent light the ballistic and snake components thereof, and wherein each of said detecting steps comprises detecting the preferentially selected light.

47. The method as claimed in claim 46 wherein said using step comprises using a difference of the light detected in steps (c) and (f) to form an image of the object in the turbid medium.

48. A method of imaging an object in a turbid medium, said method comprising the steps of:
- (a) illuminating at least a portion of the turbid medium with substantially monochromatic light of a first wavelength, said illuminated portion of the turbid medium comprising the object, wherein the light emergent from the turbid medium following illumination with said substantially monochromatic light of said first wavelength comprises a ballistic component, a snake component and a diffuse component;
- (b) wherein each of the turbid medium and the object has a resonance wavelength for an optical property, wherein the respective resonance wavelengths for the turbid medium and the object are different and wherein said substantially monochromatic light of said first wavelength is equal in wavelength to the resonance wavelength for said optical property of one of the turbid medium and the object;
- (c) preferentially passing from the emergent light the ballistic and snake components thereof;
- (d) detecting at least a portion of the light emergent from the turbid medium in response to illumination with said substantially monochromatic light of said first wavelength, wherein said detecting comprises detecting the preferentially passed light;
- (e) illuminating at least a portion of the turbid medium with substantially monochromatic light of a second wavelength, said illuminated portion of the turbid medium comprising the object, wherein the light emergent from the turbid medium following illumination with said substantially monochromatic light of said second wavelength comprises a ballistic component, a snake component and a diffuse component;

(f) wherein said substantially monochromatic light of said second wavelength is not equal in wavelength to the resonance wavelength for said optical property of either the turbid medium or the object;

(g) preferentially passing from the emergent light the ballistic and snake components thereof;

(h) detecting at least a portion of the light emergent from the turbid medium in response to illumination with said substantially monochromatic light of said second wavelength, wherein said detecting comprises detecting the preferentially passed light; and (i) using the light detected in steps (d) and (h) to form an image of the object in the turbid medium, wherein said using step comprises using a ratio of the light detected in steps (d) and (h) to form an image of the object in the turbid medium.

* * * * *